(12) United States Patent
DiLoreto et al.

(10) Patent No.: US 11,890,250 B2
(45) Date of Patent: Feb. 6, 2024

(54) INFLATABLE PENILE PROSTHESIS WITH CHANNELS IN VALVE OF GUIDE ASSEMBLY

(71) Applicant: Boston Scientific Scimed, Inc., Maple Grove, MN (US)

(72) Inventors: Mark Edward DiLoreto, Chaska, MN (US); James Ryan Mujwid, Hudson, WI (US); John Anders Bostrom, Minneapolis, MN (US); Ryan Earl Fredrick, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 222 days.

(21) Appl. No.: 17/247,342

(22) Filed: Dec. 8, 2020

(65) Prior Publication Data
US 2021/0228438 A1 Jul. 29, 2021

Related U.S. Application Data

(60) Provisional application No. 62/967,319, filed on Jan. 29, 2020.

(51) Int. Cl.
*A61H 19/00* (2006.01)

(52) U.S. Cl.
CPC ..... *A61H 19/40* (2013.01); *A61H 2201/0103* (2013.01); *A61H 2201/1246* (2013.01); *A61H 2201/5051* (2013.01)

(58) Field of Classification Search
CPC ............ A61H 19/40; A61H 2201/0103; A61H 2201/1246; A61H 2201/5051; A61F 2/484; A61F 2/26; A61F 2250/0075
See application file for complete search history.

(56) References Cited

U.S. PATENT DOCUMENTS

| 8,062,209 B2 | 11/2011 | Rowland et al. |
| 8,109,870 B2 | 2/2012 | Kuyava et al. |

(Continued)

FOREIGN PATENT DOCUMENTS

WO 2021026558 A1 2/2021

OTHER PUBLICATIONS

International Search Report and Written Opinion for PCT Application No. PCT/US2020/070890, dated Mar. 22, 2021, 12 pages.

(Continued)

*Primary Examiner* — Thaddeus B Cox
*Assistant Examiner* — Marc D. Honrath
(74) *Attorney, Agent, or Firm* — Brake Hughes Bellermann LLP

(57) ABSTRACT

An inflatable penile prosthesis can include, a reservoir, an inflatable member and a pump assembly. The pump assembly can include at least one valve comprising an entry portion, a middle portion, an exit portion, and exit tube interface, and a valve member. The exit portion can include a first landing portion including an interior portion, the interior portion of the first landing portion being semicircular about a longitudinal exit axis, the longitudinal exit axis extending through a center of the exit portion parallel to a direction that an exit tube interface extends from the exit portion, and a first channel portion adjacent to the first landing portion and including an interior portion, the interior portion of the first channel portion being farther from the longitudinal exit axis than the interior portion of the first landing portion.

20 Claims, 17 Drawing Sheets

(56) References Cited

U.S. PATENT DOCUMENTS

2007/0142700 A1* 6/2007 Fogarty ............... A61F 5/41
                                                   600/40
2010/0056859 A1  3/2010 Kuyava et al.
2013/0072751 A1* 3/2013 Fogarty ............... A61F 2/26
                                                   137/511
2019/0307567 A1* 10/2019 Mujwid ............... A61F 2/26

OTHER PUBLICATIONS

First Examination Report for Australian Application No. 2020426683, dated Feb. 6, 2023, 3 pages.

* cited by examiner

INFLATABLE PENILE PROSTHESIS WITH CHANNELS IN VALVE OF GUIDE ASSEMBLY

CROSS-REFERENCE TO RELATED APPLICATION

This application claims priority to U.S. Provisional Patent Application No. 62/967,319, filed on Jan. 29, 2020, entitled "INFLATABLE PENILE PROSTHESIS WITH CHANNELS IN VALVE OF GUIDE ASSEMBLY", the disclosure of which is incorporated by reference herein in its entirety.

TECHNICAL FIELD

This description relates to bodily implants and more specifically to bodily implants, such as a penile prosthesis that includes a refill valve and/or an inflation valve.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. In some existing devices, the pump mechanism includes a pump bulb that creates a vacuum by expanding after a manual compression, which is applied by a patient or physician. This expansion creates negative pressure (vacuum) pulling fluid through a refill valve (from the fluid reservoir to the pump bulb). Then, compression of the pump bulb results in pressure rising in the pump bulb until the point at which an inflation valve opens which allows the fluid to transfer out of the pump valve and into the inflatable cylinders. In some existing devices, which focused on maximizing efficiencies through fluid pathways, oscillation results in noise and vibration within the pump. The noise can be annoying, unnatural, and/or non-discrete to the patient.

SUMMARY

According to an example, an inflatable penile prosthesis can include a reservoir configured to hold fluid, an inflatable member, and a pump assembly configured to transfer fluid from the reservoir to the inflatable member. The pump assembly can include a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can include an entry portion defining an entry portion passageway, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising a first landing portion including an interior portion, the interior portion of the first landing portion being semicircular about a longitudinal exit axis, the longitudinal exit axis extending through a center of the exit portion parallel to a direction that an exit tube interface extends from the exit portion, and a first channel portion adjacent to the first landing portion and including an interior portion, the interior portion of the first channel portion being farther from the longitudinal exit axis than the interior portion of the first landing portion, the exit tube interface adjacent to the exit portion, the exit tube interface being configured to attach to the exit tube, the exit tube interface being narrower than the middle portion, the exit tube interface defining an exit passageway, and a valve member disposed inside the chamber, the valve member being biased to rest against the entry portion.

According to an example, an inflatable penile prosthesis can include a reservoir configured to hold fluid, an inflatable member, and a pump assembly configured to transfer fluid from the reservoir to the inflatable member. The pump assembly can include a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can include an entry portion defining an entry portion passageway, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising a first landing portion including an interior portion, the interior portion of the first landing portion being semicircular about a longitudinal exit axis, the longitudinal exit axis extending through a center of the exit portion parallel to a direction that an exit tube interface extends from the exit portion, the interior portion of the first landing portion having a landing arc, a first channel portion adjacent to the first landing portion and including an interior portion, the interior portion of the first channel portion being farther from the longitudinal exit axis than the interior portion of the first landing portion, the interior portion of the first channel portion having a channel arc, the channel arc of the first channel portion being less than the landing arc of the first landing portion, the first channel portion extending into the middle portion in a direction parallel to the longitudinal exit axis, a second landing portion adjacent to the first channel portion and including an interior portion, the interior portion of the first landing being semicircular about the longitudinal exit axis and having a landing arc that is equal to the landing arc of the interior portion of the first landing portion, and a second channel portion adjacent to the second landing portion and the first landing portion and including an interior portion, the interior portion of the second channel being farther from the longitudinal exit axis than the interior portion of the first landing portion and the interior portion of second landing portion, the interior portion of the first channel portion having a channel arc that is equal to the channel arc of the first channel portion, the first channel portion extending into the middle portion in a direction parallel to the longitudinal exit axis, the exit tube interface adjacent to the exit portion, the exit tube interface being configured to attach to the exit tube, the exit tube interface being narrower than the middle portion, the exit tube interface defining an exit passageway, and a valve member disposed inside the chamber, the valve member being biased to rest against the entry portion.

According to an example, an inflatable penile prosthesis can include a reservoir configured to hold fluid, an inflatable member, and a pump assembly configured to transfer fluid from the reservoir to the inflatable member. The pump assembly can include a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed. The at least one valve can include an entry portion defining an entry portion passageway, a middle portion adjacent to the entry portion, the middle portion being wider than the entry portion and defining a chamber, an exit portion adjacent to the middle portion, the exit portion being narrower than the middle portion, the exit portion defining an exit portion passageway and comprising a first landing portion including an interior portion, the interior portion of the first landing portion being semicircular about a longitudinal exit axis, the longitudinal exit axis extending through a center of the exit portion parallel to a direction that an exit tube interface extends from the exit portion, the interior portion of the first landing portion having a landing arc, a first channel portion adjacent to the first landing portion and including an interior portion, the interior portion of the first channel portion being farther from the longitudinal exit axis than the interior portion of the first landing portion, the interior portion of the first channel portion having a channel arc, the channel arc of the first channel portion being less than the landing arc of the first landing portion, the first channel portion extending into the middle portion along a path that curves with respect to the longitudinal exit axis, a second landing portion adjacent to the first channel portion and including an interior portion, the interior portion of the first landing being semicircular about the longitudinal exit axis and having a landing arc that is equal to the landing arc of the interior portion of the first landing portion, and a second channel portion adjacent to the second landing portion and the first landing portion and including an interior portion, the interior portion of the second channel being farther from the longitudinal exit axis than the interior portion of the first landing portion and the interior portion of second landing portion, the interior portion of the first channel portion having a channel arc that is equal to the channel arc of the first channel portion, the first channel portion extending into the middle portion along a path that curves with respect to the longitudinal exit axis, the exit tube interface adjacent to the exit portion, the exit tube interface being configured to attach to the exit tube, the exit tube interface being narrower than the middle portion, the exit tube interface defining an exit passageway, and a valve member disposed inside the chamber, the valve member being biased to rest against the entry portion.

The details of one or more implementations are set forth in the accompanying drawings and the description below. Other features will be apparent from the description and drawings, and from the claims.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The terms "including" and/or "having", as used herein, are defined as comprising (i.e., open transition).

In general, the embodiments are directed to medical devices such as penile prostheses or other bodily implants. The term patient may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein provide a valve within an inflatable penile prosthesis that can reduce noise due to oscillation of a valve member, such as a poppet, within the valve.

Figure 1:
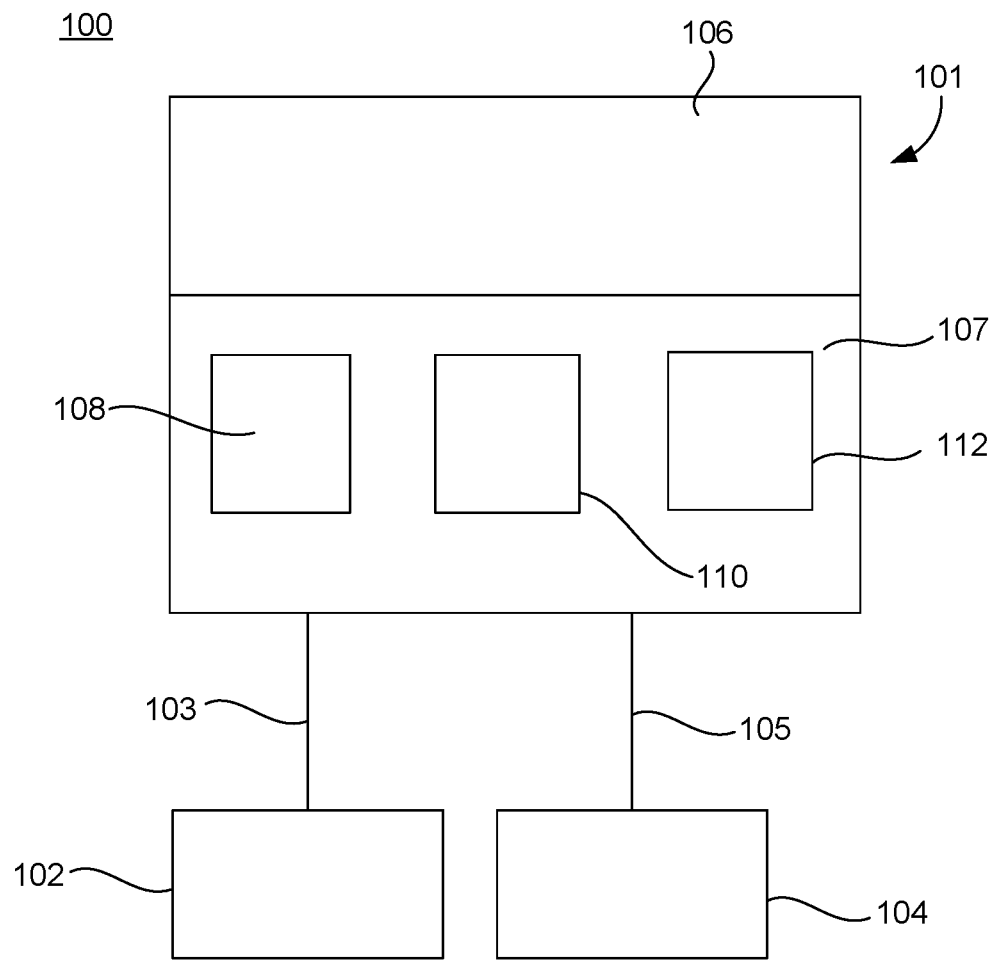
FIG. 1 schematically illustrates a penile prosthesis according to an aspect.

FIG. 1 schematically illustrates a penile prosthesis 100 according to an aspect. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the patent, the reservoir 102 may be implanted in the abdomen or pelvic cavity of the patient (e.g., the reservoir 102 may be implanted in the lower portion of the patient's abdominal cavity or the upper portion of the patient's pelvic cavity), and the pump assembly 101 may be implanted in the scrotum of the patient.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. The conduit connectors 103, 105 can also be considered an entry tube for carrying fluid into a valve (described below) and an exit tube for carrying fluid from a valve. Each of the first conduit connector 103 and the second conduit connector 105 can define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 can be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 can include a single or multiple tube members for transferring the fluid between the pump assembly 101 and the inflatable member 104. In some examples, the first conduit connector 103 and the second conduit connector 105 can include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 can include a pump bulb 106 and at least one valve, such as a valve body 107. In some examples, the pump bulb 106 may include a flexible member defining a cavity. In some examples, the pump bulb 106 may define a pump shell having a flexible bulb and a valve body connector, where the valve body connector is designed to fit at least partially over the valve body 107. In some examples, the pump bulb 106 may include a squeeze pump. In some examples, the pump bulb 106 may include a portion that is round or substantially round. In some examples, the pump bulb 106 may include ribbing or dimples to aid the patient in gripping the pump bulb 106. The pump bulb 106 may use suction and pressure to move the fluid in and out of the cavity of the pump bulb 106 in the inflation mode. For example, the patient may depress or squeeze the pump bulb 106 to expel the fluid out of the cavity, and, when the flexible member returns to its original shape, the resulting suction pushes the fluid into the cavity of the pump bulb 106. In some examples, the pump bulb 106 may have a bulb spring rate that is designed to refill the pump bulb 106 in a selected time frame.

The pump bulb 106 may be squeezed or depressed by the patient in order to facilitate the transfer of fluid from the reservoir 102 to the inflatable member 104. For example, in the inflation mode, while the patient is operating the pump bulb 106, the pump bulb 106 may receive the fluid from the reservoir 102, and then output the fluid to the inflatable member 104. When the patient switches the pump bulb 106 to the deflation mode, at least some of the fluid can automatically be transferred back to the reservoir 102 (due to the difference in pressure from the inflatable member 104 to the reservoir 102). Then, the patient may squeeze the inflatable member 104 to facilitate the further transfer of fluid through the pump bulb 106 to the reservoir 102.

The valve body 107 can include at least one valve, such as a refill valve 108, an inflation valve 110, and/or a deflation valve 112. The valve body 107 may define a first fluid passageway that connects the pump bulb 106 to the first conduit connector 103. The first fluid passageway may be a cavity that extends through the valve body 107. The first fluid passageway may define a cylindrical cavity having sections with different diameters. The refill valve 108 is disposed within at least one of the sections of the first fluid passageway. The valve body 107 may define a second fluid passageway that connects the pump bulb 106 to the second conduit connector 105. The second fluid passageway may be a cavity that extends through the valve body 107. The second fluid passageway is separate from the first fluid passageway. The second fluid passageway may define a cylindrical cavity having sections with different diameters. The inflation valve 110 is disposed within at least one of the sections of the second fluid passageway.

The refill valve 108 moves within the first fluid passageway between an open position and a closed position (or sealing position). The refill valve 108 can include a biasing member to return a valve member, such as a poppet, to the sealing position. The biasing member can bias the refill valve to the closed and/or sealed position. Fluid flowing from the reservoir 102 to the pump bulb 106 can overcome the force of the biasing member and move the refill valve to an open position, allowing fluid to flow through the refill valve 108. Fluid flowing from the pump bulb 106 to the reservoir 102, or no fluid flowing through the refill valve 108, can cause the refill valve 108 to close and/or seal.

The inflation valve 110 moves within the second fluid passageway between an open position and a closed position (or sealing position), and a biasing member is used to bias the inflation valve 110 to the sealing position. In some examples, the biasing member is a spring. The inflation valve 110 may provide a reliable seal in order to maintain fluid pressure within the inflatable member 104, but also allow fluid in during inflation of the inflatable member 104. The pump bulb 106 can transfer the fluid from the reservoir 102, through the at least one valve 108, 110, and to the inflatable member 104 in response to the pump bulb 106 being compressed. When the patient compresses the pump bulb 106, the pressure increases within the pump bulb 106 and eventually opens the inflation valve 110, thereby allowing fluid to pass over the inflation valve 110. The initial opening of the inflation valve 110 requires compression of the pump bulb 106, resulting in a pressure spike that opens the inflation valve 110. Keeping the inflation valve 110 open is dependent on the pressure differential over the inflation valve seat, which is determined by the application of force by the patient in addition to spring preload/rate and downstream flow resistance.

In some examples, the valve body 107 includes the deflation valve 112. The deflation valve 112 can also be considered an anti-auto inflation valve. In some examples, the deflation valve 112 allows the fluid to flow from the inflatable member 104 back to the reservoir 102 when the pump assembly 101 is in the deflation mode. In some examples, the deflation valve prevents fluid from flowing from the reservoir 102 to the inflatable member 104 when the pump assembly 101 is in the deflation mode.

Figure 2A:
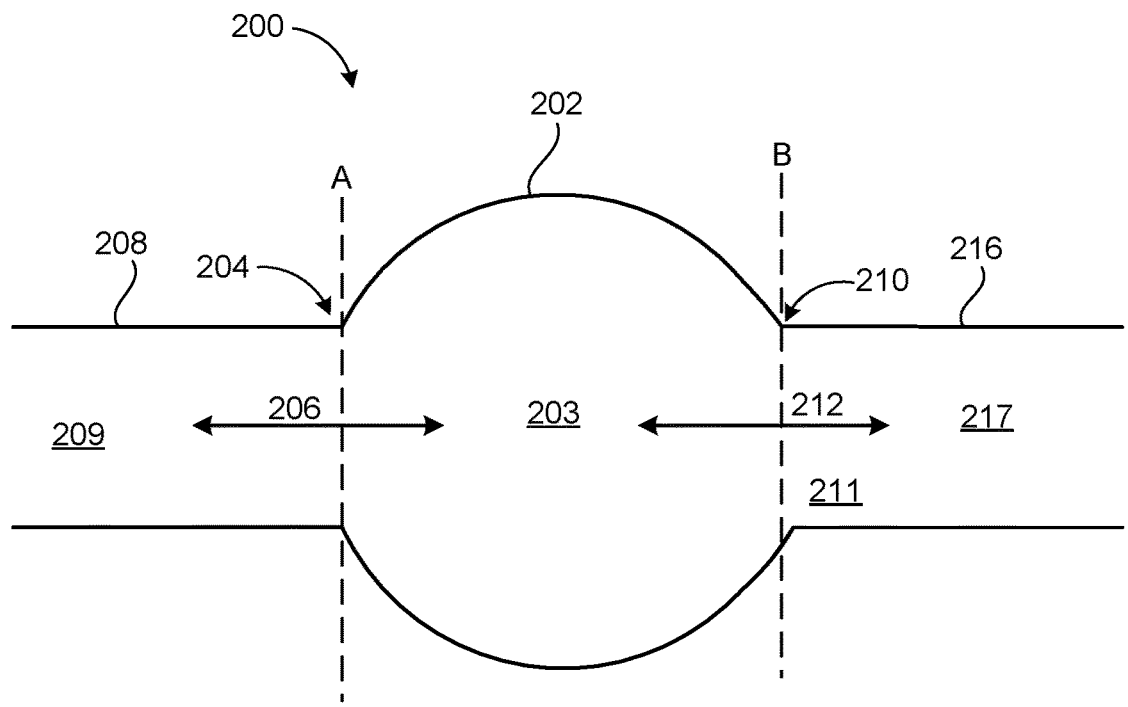
FIG. 2A illustrates a valve included in the penile prosthesis according to an aspect.

FIG. 2A illustrates a valve 200 included in the penile prosthesis 100 according to an aspect. The valve 200 can be an example of either the refill valve 108 or the inflation valve 110. FIG. 2A is a cross-sectional view of the valve 200.

The valve 200 can include an entry tube interface 208, a base 204 and/or entry portion adjacent to the entry tube interface 208, a bulb 202 and/or middle portion adjacent to the base 204, a tail 210 and/or exit portion adjacent to the bulb 202, and an exit tube interface 216 adjacent to the tail 210.

The entry tube interface 208 can be configured to attach to, and/or can be attached to, an entry tube. The entry tube can carry fluid into the valve 200, and can include either of the first or second conduit connectors 103, 105 (shown in FIG. 1). The entry tube interface 208 can be narrower than the bulb 202. The entry tube interface 208 can define an entry passageway 209 via which fluid can flow into the valve 200 and/or bulb 202 from the entry tube.

The base 204 can be circular about a longitudinal base axis 206 and/or longitudinal entry portion axis. The longitudinal base axis 206 can extend parallel to a direction in which the entry tube interface 208 extends from the base 204. The base 204 can define a base passageway 205 (labeled in FIG. 2C) and/or entry portion passageway. Fluid can flow between the entry passageway 209 and the bulb 202 via the base passageway 205. A valve member 218 such as a poppet (shown in FIG. 2B) can rest against the base 204, closing and/or sealing the valve 200.

The bulb 202 can be wider than both the entry tube interface 208 and the exit tube interface 216. The bulb 202 can define a chamber 203. The valve member 218 can reside in the chamber 203. Fluid can flow through the chamber 203 from the entry tube interface 208 into the exit tube interface 216.

The tail 210 can be narrower than the bulb 202. The tail 210 can define a tail passageway 211 (labeled in FIGS. 3A, 4A, 5A, and 6A) and/or exit portion passageway through which fluid can flow between the chamber 203 and an exit passageway 217 defined by the exit tube interface 216.

The tail 210 can include one or more landing portions and channel portions, shown and described with respect to subsequent figures. The landing portions and channel portions can extend into the chamber 203, into the tail passageway 211, and/or about a longitudinal tail axis 212. The longitudinal tail axis 212 can extend through a center of the tail 210 parallel to a direction that the exit tube interface 216 extends from the tail 210.

The exit tube interface 216 can be configured to attach to, and/or can be attached to, an exit tube. The exit tube can carry fluid from the valve 200, and can include either of the first or second conduit connectors 103, 105. The exit tube interface 216 can be narrower than the bulb 202. The exit tube interface 216 can define an exit passageway 217 via which fluid can flow from the valve 200 and/or bulb 202 to the exit tube. The entry passageway 209, base passageway 205, chamber 203, tail passageway 211, and exit passageway 217 can collectively form a first or second fluid passageway described above with respect to FIG. 1.

Figure 2B:
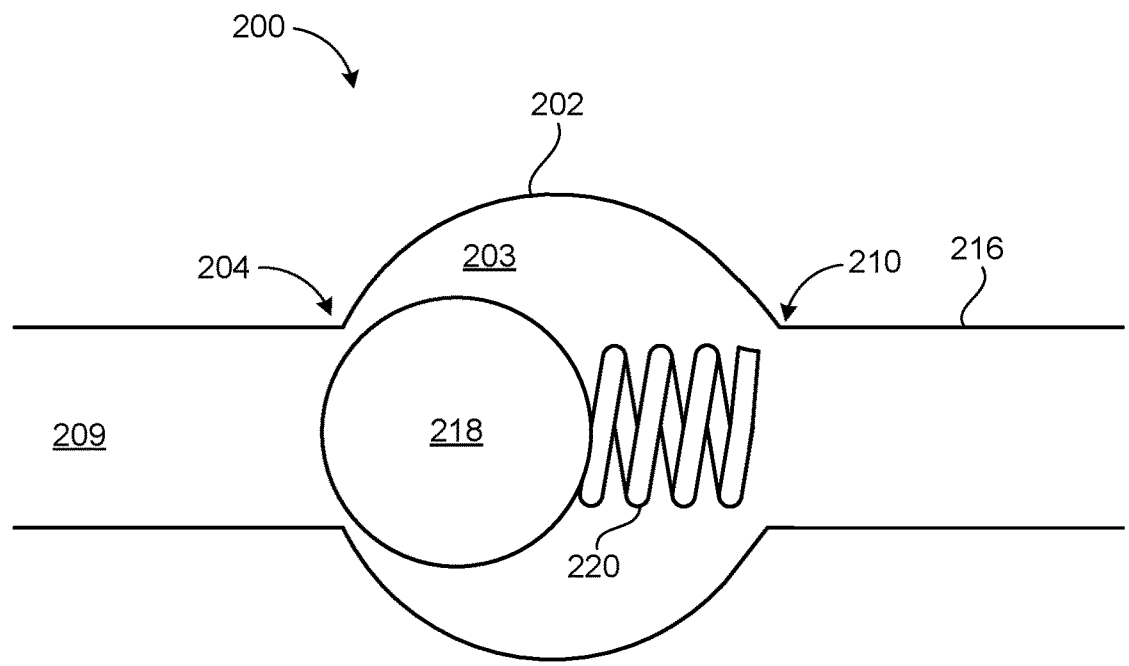
FIG. 2B illustrates the valve according to another aspect.

FIG. 2B illustrates the valve 200 according to another aspect. FIG. 2B is the same cross-sectional view of the valve 200 as FIG. 2A.

The poppet 218 can be included in the chamber 203. The poppet 218 can include at least one rounded portion that contacts and/or seals with the base 204, sealing and/or closing the valve 200. The poppet 218 can include various shapes, such as spherical, having a spherical member and a partial cone member extending from the spherical member, a cap member with a rounded portion facing toward the base 204 and a flat portion facing toward the tail 210 and a stem extending from the flat portion of the cap member, a spherical member with a cylindrical member extending from the spherical member and a partial cone member extending from the cylindrical member, or a cap member with a rounded portion and one or two stems extending from the cap member, as non-limiting examples. In some examples, the poppet 218 can include one or more grooves.

The valve 200 can include a biasing member 220. The biasing member 220 can include a coil and/or spring. The biasing member 220 can be at least partially disposed within the chamber 203. The biasing member 220 can press and/or bias the valve member 218 and/or poppet toward and/or against the base 204, placing the valve 200 in the sealed and/or closed position, as described above with respect to FIG. 1A. The poppet 218 can press against the base 204 until fluid pressure from the entry passageway 209 presses the poppet 218 away from the base 204 toward the tail 210, opening the valve 200 and/or moving the valve 200 into the open position, as described above with respect to FIG. 1. The biasing member 220 can be secured to the tail, or other component of the valve 200.

Figure 2C:
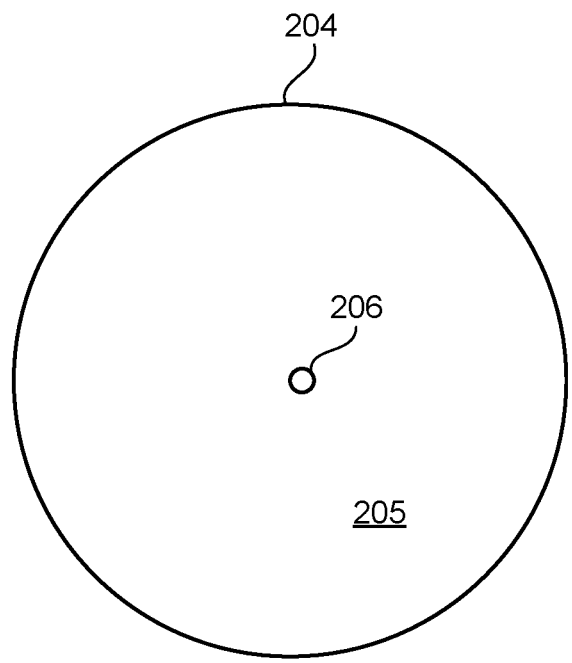
FIG. 2C illustrates the valve according to another aspect.

FIG. 2C illustrates the valve according to another aspect. FIG. 2C is a cross-sectional view of the valve 200 along the line denoted 'A' in FIG. 2A. The base 204 can define the base passageway 205. The base axis 206 can extend through a center of the base 204.

Figure 3A:
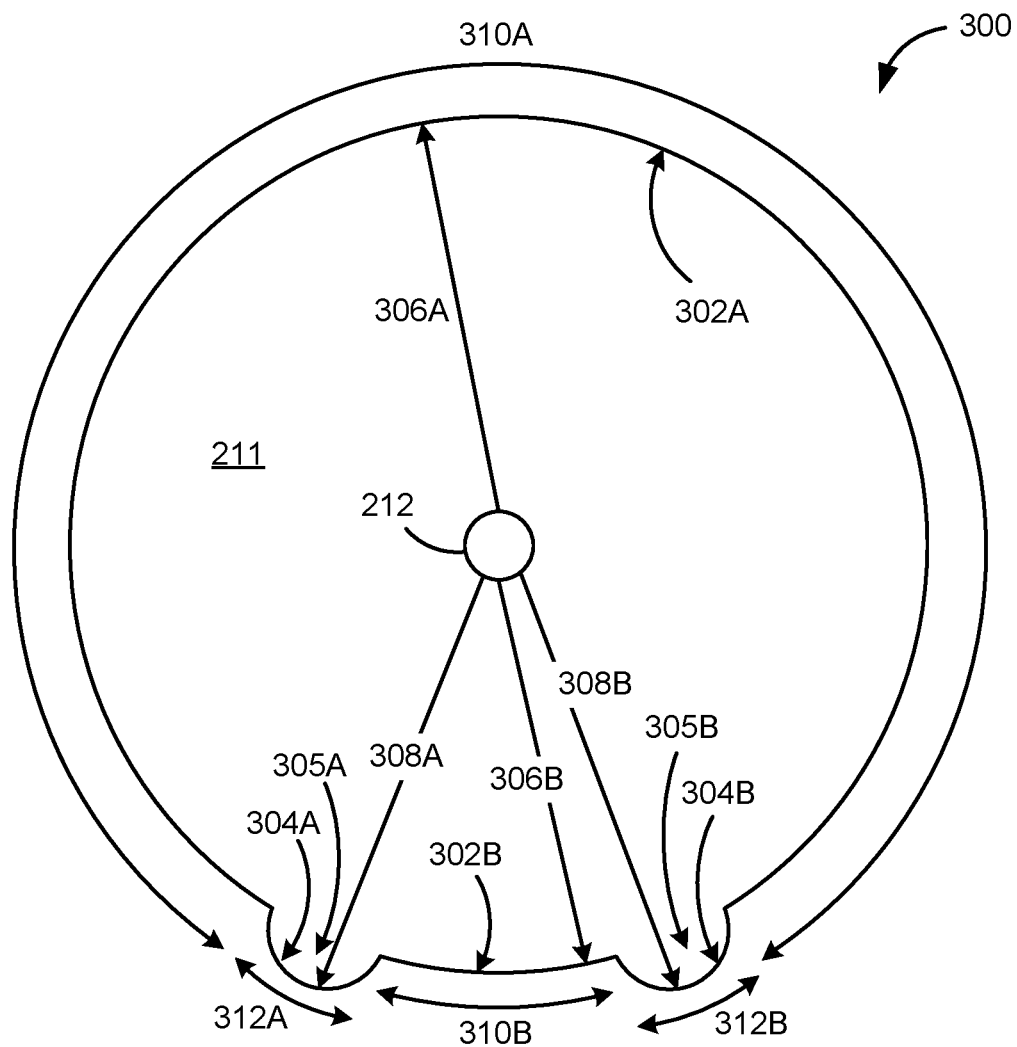
FIG. 3A illustrates a valve according to an aspect.

FIG. 3A illustrates a valve 300 according to an aspect. The valve 300 can include any combination of features of the valve 200 described above. FIG. 3A is a cross-sectional view of the valve 200, 300 along the line denoted 'B' in FIG. 2A. FIG. 3A shows components of the tail 210 and/or exit portion.

The valve 300 and/or tail 210 can include at least a first landing portion 302A and a first channel portion 304B defining a channel 305A. In some examples, the valve 300 and/or tail 210 can include a first landing portion 302A and a second landing portion 302B. In some examples, the valve 300 and/or tail 210 can include a first channel portion 304A defining a first channel 305A within the tail passageway 211 and a second channel portion 304B defining a second channel 305B within the tail passageway 211. The first landing portion 302A can be adjacent to, and/or disposed between, the first channel portion 304A and the second channel portion 304B. The first channel portion 304A can be adjacent to, and/or disposed between, the first landing portion 302A and the second landing portion 302B. The second landing portion 302B can be adjacent to, and/or disposed between, the first channel portion 304A and the second channel portion 304B. The second channel portion 304B can be adjacent to, and/or disposed between, the first landing portion 302A and the second landing portion 302B.

When the valve 300 is in the open position, with the valve member 218 and/or poppet resting on and/or pressing against the tail 210 and/or exit portion, the valve member 218 can rest on and/or press against the landing portion(s) 302A, 302B), and fluid can pass through channels 305A, 305B defined by channel portion(s) 304A, 304B.

The first landing portion 302A and/or second landing portion 302B can be semicircular about the longitudinal exit axis 212. A distance(s) 308A, 308B of an interior portion(s) of the channel portion(s) 304A, 304B from the longitudinal axis 212 can be greater than a distance(s) 306A, 306B and/or radius of an interior portion(s) of the landing portion(s) 302A, 302B from the longitudinal axis 212, and/or the distance(s) 306A, 306B of the interior portion(s) of the landing portion(s) 302A, 302B can be less than the distance(s) 306A, 306B of the interior portion(s) of the landing portion(s) 302A, 302B from the longitudinal axis 212. The greater distance(s) of the interior portion(s) of the channel portion(s) 304A, 304B creates and/or defines the channel(s) 305A, 305B for the fluid to flow through.

In some examples, a radius, which can be considered a landing radius and/or landing distance 306A from the longitudinal exit axis 212, of the inner portion of the first landing portion 302A, can be equal to a radius, and/or distance 306B from the longitudinal exit axis 212, of the inner portion of the second landing portion 302B. In some examples, an arc 310A, which can be considered a landing arc, of the first landing portion 302A can be greater than an arc 310B of the second landing portion 302B. In some examples, the arc 310A of the first landing portion 302A can be greater than an arc 312A, which can be considered a channel arc, of the first channel portion 304A. In some examples, the arc 310A of the first landing portion 302A can be greater than an arc 312B of the second channel portion 304B. In some examples, the arc 310B of the second landing portion 302B can be greater than an arc 312B of the second channel portion 304B. In some examples, the arc 310B of the second landing portion 302B can be greater than an arc 312B of the second channel portion 304B. In some examples, the arc 312A of the first channel portion 304A can be equal to the arc 312B of the second channel portion 304B.

Figure 3B:
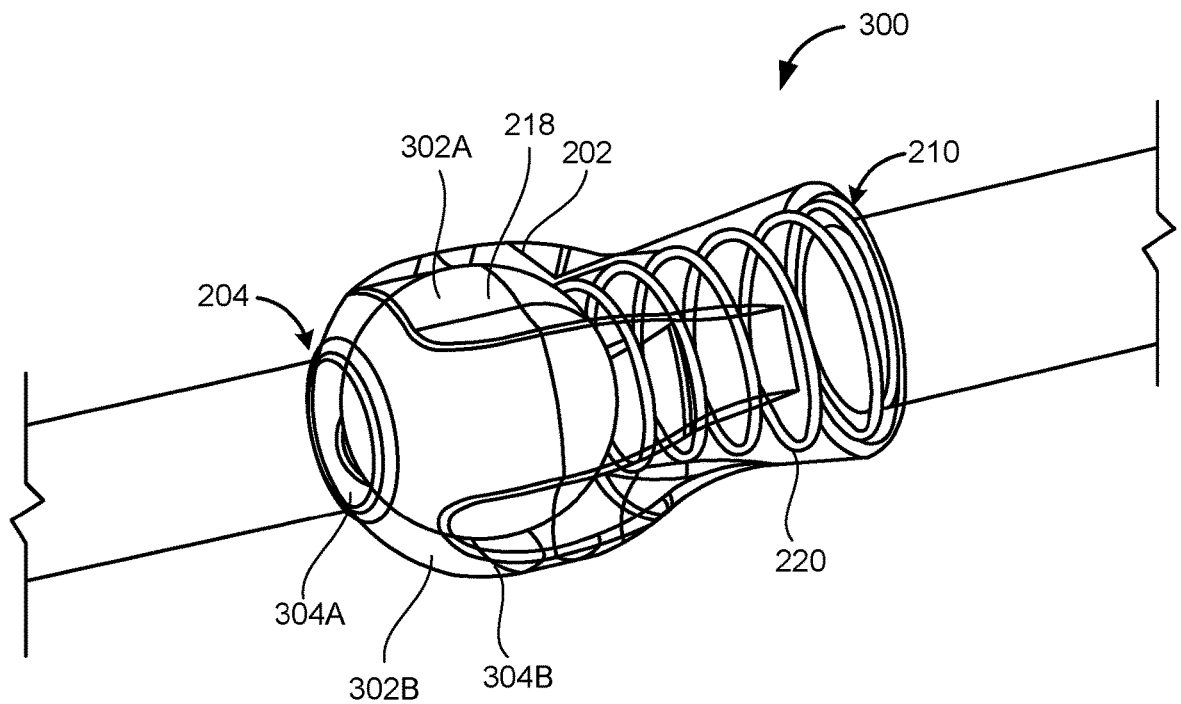
FIG. 3B illustrates the valve of FIG. 3A according to an aspect.

FIG. 3B illustrates the valve 300 of FIG. 3A according to an aspect. In this example, the landing portions 302A, 302B and channel portions 304A, 304B extend from the bulb 202 and/or middle portion to and/or through the tail 210 and/or exit portion. The valve member 218 can be disposed inside the bulb 202.

Figure 3C:
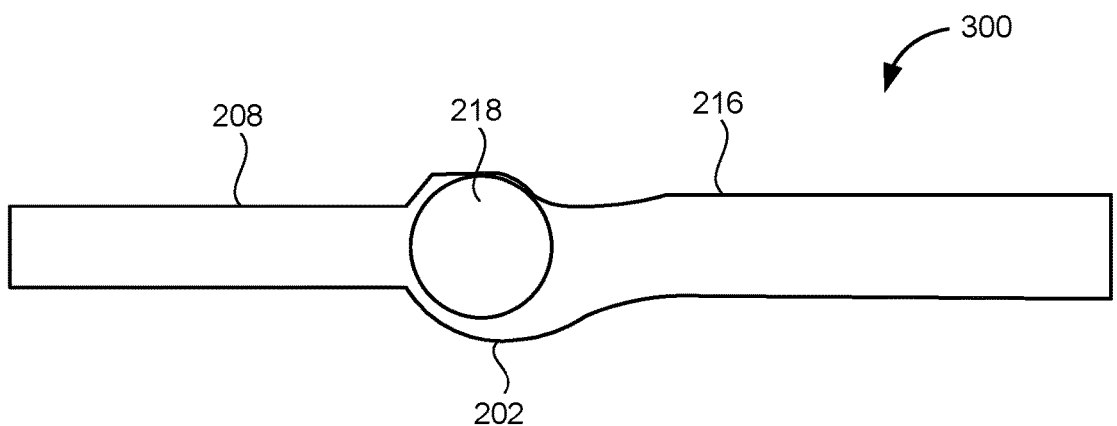
FIG. 3C illustrates the valve of FIGS. 3A and 3B according to an aspect.

FIG. 3C illustrates the valve 300 of FIGS. 3A and 3B according to an aspect. The valve 300 can include any combination of features of the valve 200, 300 described above, such as the entry tube interface 208, bulb 202, valve member, and exit tube interface 216.

Figure 4A:
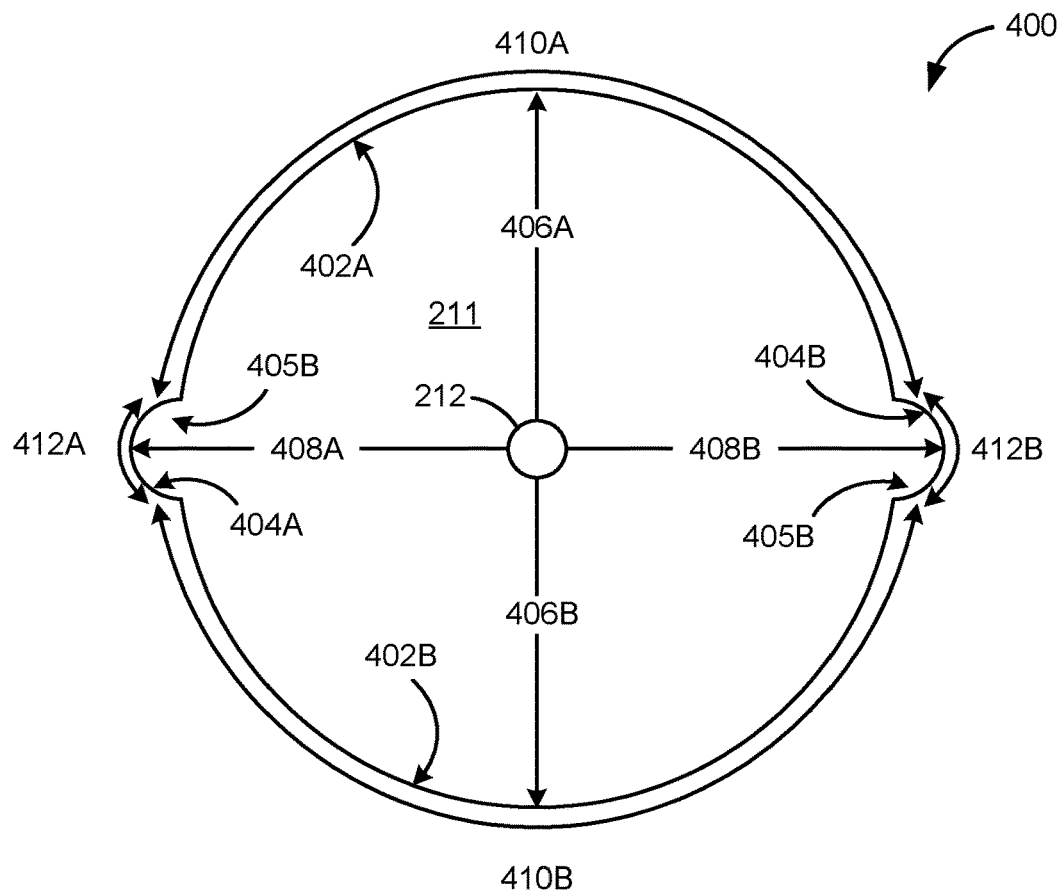
FIG. 4A illustrates a valve according to an aspect.

FIG. 4A illustrates a valve 400 according to an aspect. The valve 400 can include any combination of features of the valve 200 described above. FIG. 4A is a cross-sectional view of the valve 200, 400 along the line denoted 'C' in FIG. 4C. FIG. 4A shows components of the tail 210 and/or exit portion.

The valve 400 and/or tail 210 can include at least a first landing portion 402A and a first channel portion 404B defining a channel 405A. In some examples, the valve 400 and/or tail 210 can include a first landing portion 402A and a second landing portion 402B. In some examples, the valve 400 and/or tail 210 can include a first channel portion 404A defining a first channel 405A within the tail passageway 211 and a second channel portion 404B defining a second channel 405B within the tail passageway 211. The first landing portion 402A can be adjacent to, and/or disposed between, the first channel portion 404A and the second channel portion 404B. The first channel portion 404A can be adjacent to, and/or disposed between, the first landing portion 402A and the second landing portion 402B. The second landing portion 402B can be adjacent to, and/or disposed between, the first channel portion 404A and the second channel portion 404B. The second channel portion 404B can be adjacent to, and/or disposed between, the first landing portion 402A and the second landing portion 402B.

When the valve 400 is in the open position, with the valve member 218 and/or poppet resting on and/or pressing against the tail 210 and/or exit portion, the valve member 218 can rest on and/or press against the landing portion(s) 402A, 402B), and fluid can pass through channels 405A, 405B defined by channel portion(s) 404A, 404B.

The first landing portion 402A and/or second landing portion 402B can be semicircular about the longitudinal exit axis 212. A distance(s) 408A, 408B of an interior portion(s) of the channel portion(s) 404A, 404B from the longitudinal axis 212 can be greater than a distance(s) 406A, 406B of an interior portion(s) of the landing portion(s) 402A, 402B from the longitudinal axis 212, and/or the distance(s) 406A, 406B of the interior portion(s) of the landing portion(s) 402A, 402B can be less than the distance(s) 406A, 406B of the interior portion(s) of the landing portion(s) 402A, 402B from the longitudinal axis 212. The greater distance(s) of the interior portion(s) of the channel portion(s) 404A, 404B creates and/or defines the channel(s) 405A, 405B for the fluid to flow through.

In some examples, a radius, and/or distance 406A from the longitudinal exit axis 212, of the inner portion of the first landing portion 402A, can be equal to a radius, and/or distance 406B from the longitudinal exit axis 212, of the inner portion of the second landing portion 402B. In some examples, an arc 410A of the first landing portion 402A can be equal to an arc 410B of the second landing portion 402B. In some examples, the arc 410A of the first landing portion 402A can be greater than an arc 412A of the first channel portion 404A. In some examples, the arc 410A of the first landing portion 402A can be greater than an arc 412B of the second channel portion 404B. In some examples, the arc 410B of the second landing portion 402B can be greater than an arc 412B of the second channel portion 404B. In some examples, the arc 410B of the second landing portion 402B can be greater than an arc 412B of the second channel portion 404B. In some examples, the arc 412A of the first channel portion 404A can be equal to the arc 412B of the second channel portion 404B. In some examples, the arc(s) 410A, 410B of the first and second landing portions can each be less than one hundred and eighty degrees (180°). In some examples, the arc(s) 410A, 410B of the first and second landing portions can each be greater than ninety degrees (90°).

In some examples, any combination of the landing portions(s) 402A, 402B and/or channel portions(s) 404A, 404B can curve with respect to the longitudinal exit axis 212. The curving of the landing portions(s) 402A, 402B and/or channel portions(s) 404A, 404B with respect to the longitudinal exit axis 212 can cause the channel portion(s) 404A, 404B to have a vortex and/or spiral shape.

Figure 4B:
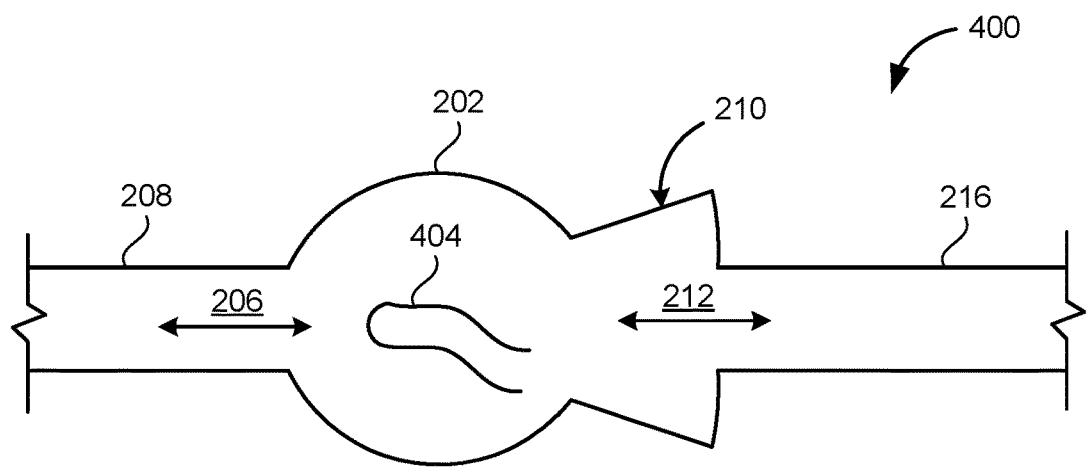
FIG. 4B illustrates the valve of FIG. 4A according to an aspect.

FIG. 4B illustrates the valve of FIG. 4A according to an aspect. FIG. 4 shows a channel portion 404, which can represent either of the channel portions 404A, 404B shown and described with respect to FIG. 4A, with a curved, spiral, and/or vortex shape. The curved channel portion(s) 404 can curve with respect to the longitudinal entry axis 206 and/or with respect to the longitudinal exit axis 212. The curved channel portion(s) 404 can be included in, and/or extend within, the bulb 202 and/or tail 210.

Figure 4C:
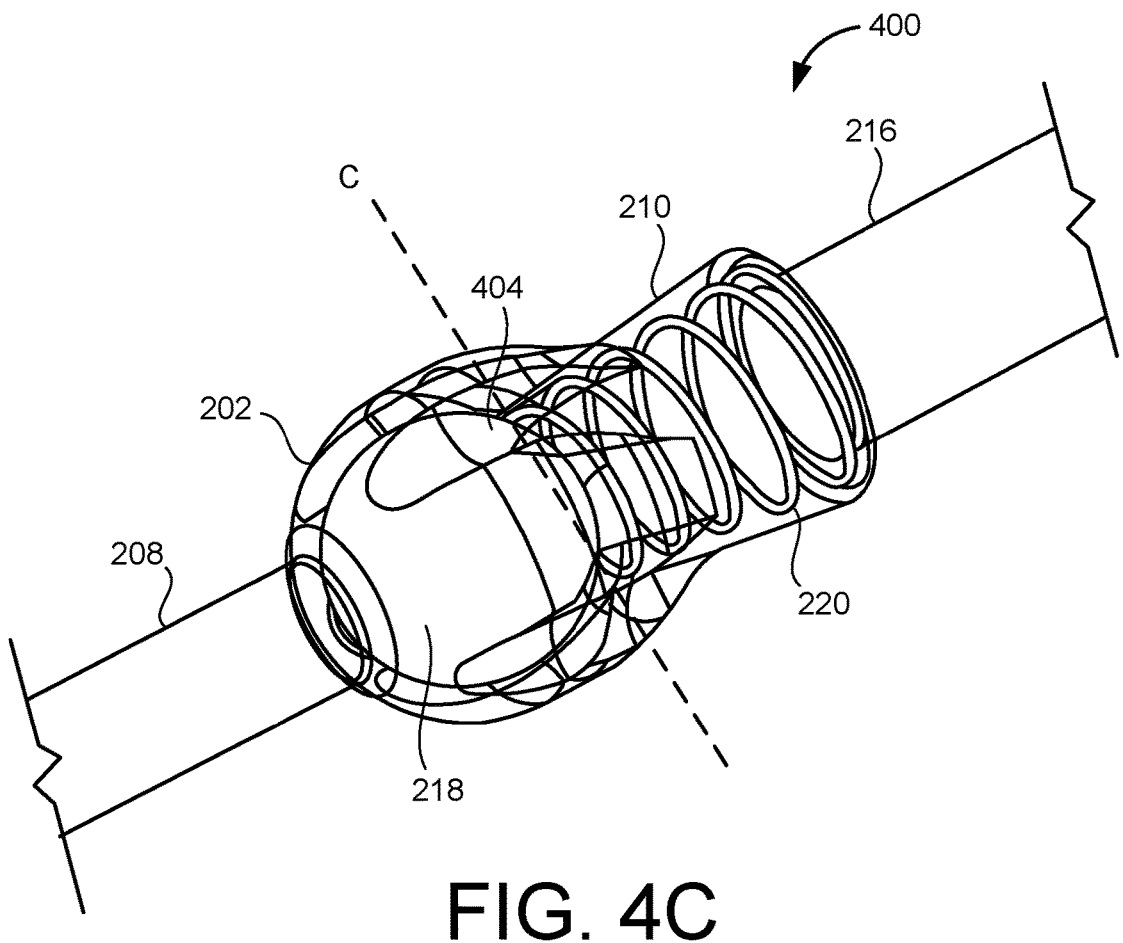
FIG. 4C illustrates the valve of FIGS. 4A and 4B according to an aspect.

FIG. 4C illustrates the valve of FIGS. 4A and 4B according to an aspect. FIG. 4C shows the curved channel 404 extending within the bulb 202 and base 210.

Figure 4D:
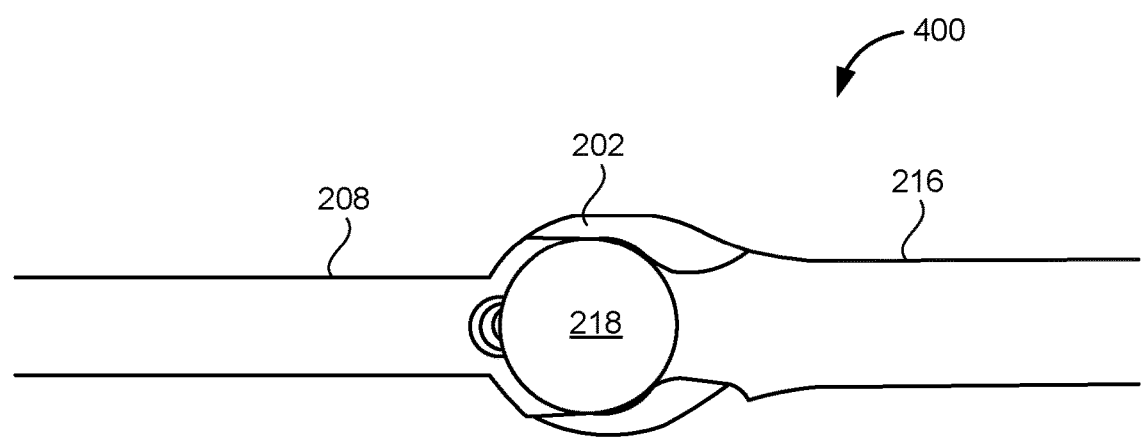
FIG. 4D illustrates the valve of FIGS. 4A, 4B, and 4C according to an aspect.

FIG. 4D illustrates the valve 400 of FIGS. 4A, 4B, and 4C according to an aspect. FIG. 4D shows the valve member 218 within the bulb 202, the entry tube interface 208, and the exit tube interface 216.

Figure 5A:
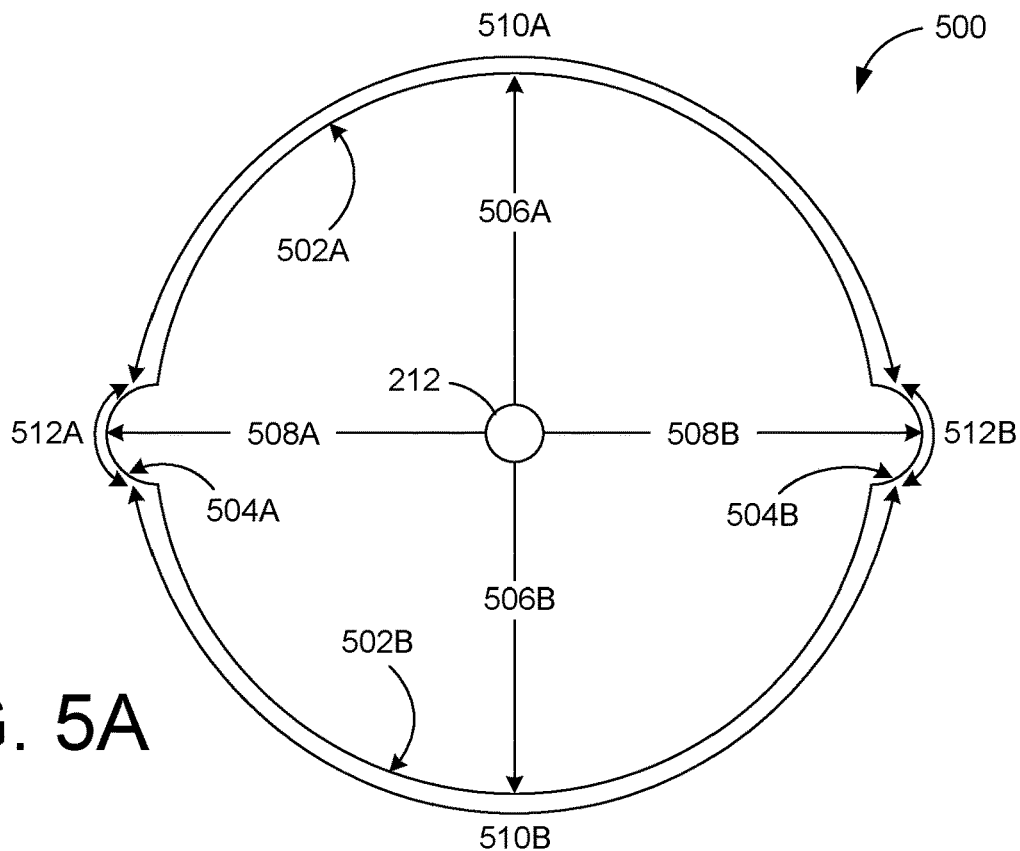
FIG. 5A illustrates a valve according to an aspect.

FIG. 5A illustrates a valve 500 according to an aspect. The valve 500 can include any combination of features of the valve 200 described above. FIG. 5A is a cross-sectional view of the valve 200, 500 along the line denoted 'D' in FIG. 5C. FIG. 5A shows components of the tail 210 and/or exit portion.

The valve 500 and/or tail 210 can include at least a first landing portion 502A and a first channel portion 504B defining a channel 505A. In some examples, the valve 500 and/or tail 210 can include a first landing portion 502A and a second landing portion 502B. In some examples, the valve 500 and/or tail 210 can include a first channel portion 504A defining a first channel 505A within the tail passageway 211 and a second channel portion 504B defining a second channel 505B within the tail passageway 211. The first landing portion 502A can be adjacent to, and/or disposed between, the first channel portion 504A and the second channel portion 504B. The first channel portion 504A can be adjacent to, and/or disposed between, the first landing portion 502A and the second landing portion 502B. The second landing portion 502B can be adjacent to, and/or disposed between, the first channel portion 504A and the second channel portion 504B. The second channel portion 504B can be adjacent to, and/or disposed between, the first landing portion 502A and the second landing portion 502B.

When the valve 500 is in the open position, with the valve member 218 and/or poppet resting on and/or pressing against the tail 210 and/or exit portion, the valve member 218 can rest on and/or press against the landing portion(s) 502A, 502B), and fluid can pass through channels 505A, 505B defined by channel portion(s) 504A, 504B.

The first landing portion 502A and/or second landing portion 502B can be semicircular about the longitudinal exit axis 212. A distance(s) 508A, 508B of an interior portion(s) of the channel portion(s) 504A, 504B from the longitudinal axis 212 can be greater than a distance(s) 506A, 506B of an interior portion(s) of the landing portion(s) 502A, 502B from the longitudinal axis 212, and/or the distance(s) 506A, 506B of the interior portion(s) of the landing portion(s) 502A, 502B can be less than the distance(s) 506A, 506B of the interior portion(s) of the landing portion(s) 502A, 502B from the longitudinal axis 212. The greater distance(s) of the interior portion(s) of the channel portion(s) 504A, 504B creates and/or defines the channel(s) 505A, 505B for the fluid to flow through.

In some examples, a radius, and/or distance 506A from the longitudinal exit axis 212, of the inner portion of the first landing portion 502A, can be equal to a radius, and/or distance 506B from the longitudinal exit axis 212, of the inner portion of the second landing portion 502B. In some examples, an arc 510A of the first landing portion 502A can be equal to an arc 510B of the second landing portion 502B. In some examples, the arc 510A of the first landing portion 502A can be greater than an arc 512A of the first channel portion 504A. In some examples, the arc 510A of the first landing portion 502A can be greater than an arc 512B of the second channel portion 504B. In some examples, the arc 510B of the second landing portion 502B can be greater than an arc 512B of the second channel portion 504B. In some examples, the arc 510B of the second landing portion 502B can be greater than an arc 512B of the second channel portion 504B. In some examples, the arc 512A of the first channel portion 504A can be equal to the arc 512B of the second channel portion 504B. In some examples, the arc(s) 510A, 510B of the first and second landing portions can each be less than one hundred and eighty degrees (180°). In some examples, the arc(s) 510A, 510B of the first and second landing portions can each be greater than ninety degrees (90°).

In some examples, any combination of the landing portions(s) 502A, 502B and/or channel portions(s) 504A, 504B can extend along the bulb and/or tail 210 in a direction parallel to the longitudinal exit axis 212. The straight extension of the landing portions(s) 502A, 502B and/or channel portions(s) 504A, 504B, parallel to the longitudinal exit axis 212, can cause the fluid to flow in a straight path.

Figure 5B:
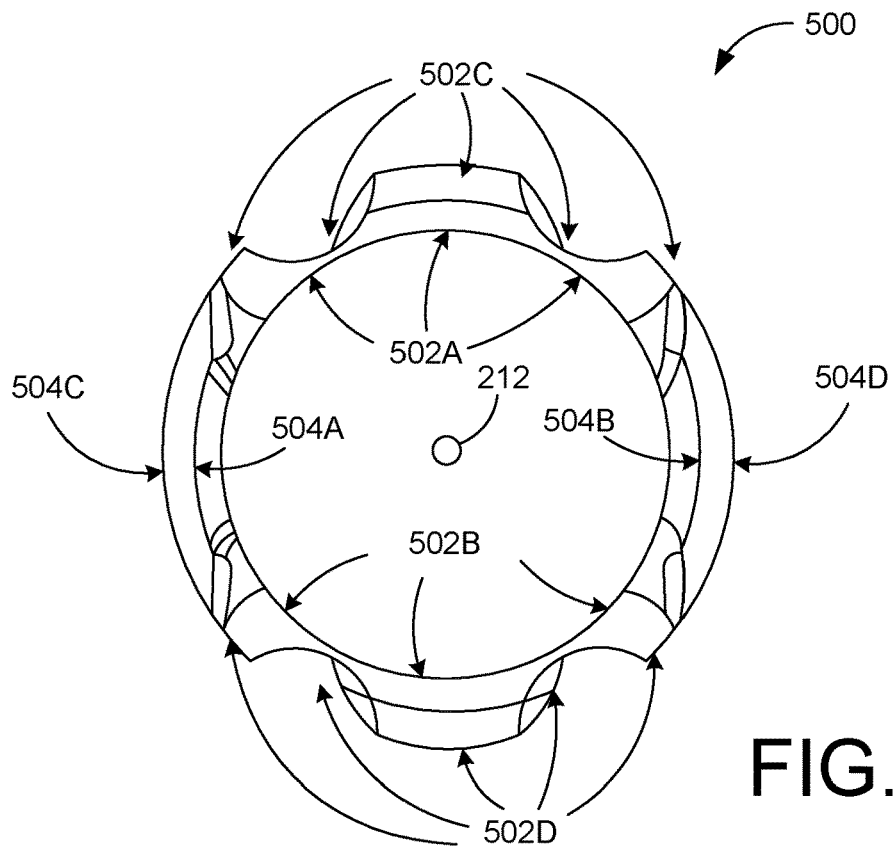
FIG. 5B illustrates the valve of FIG. 5A according to an aspect.

FIG. 5B illustrates the valve 500 of FIG. 5A according to an aspect. In this example, the inner portions of the landing portions 502A, 502B are semicircular about the longitudinal exit axis 212. In this example, the inner portions of the channel portions 504A, 504B are farther from the longitudinal exit axis 212 than the inner portions of the landing portions 502A, 502B.

In this example, outer portions 502C, 502D of the landing portions 502A, 502B are ridged, and/or alternate peaks and valleys. In this example, outer portions 504C, 504D of the channel portions 504A, 504B are semicircular about the longitudinal exit axis 212.

Figure 5C:
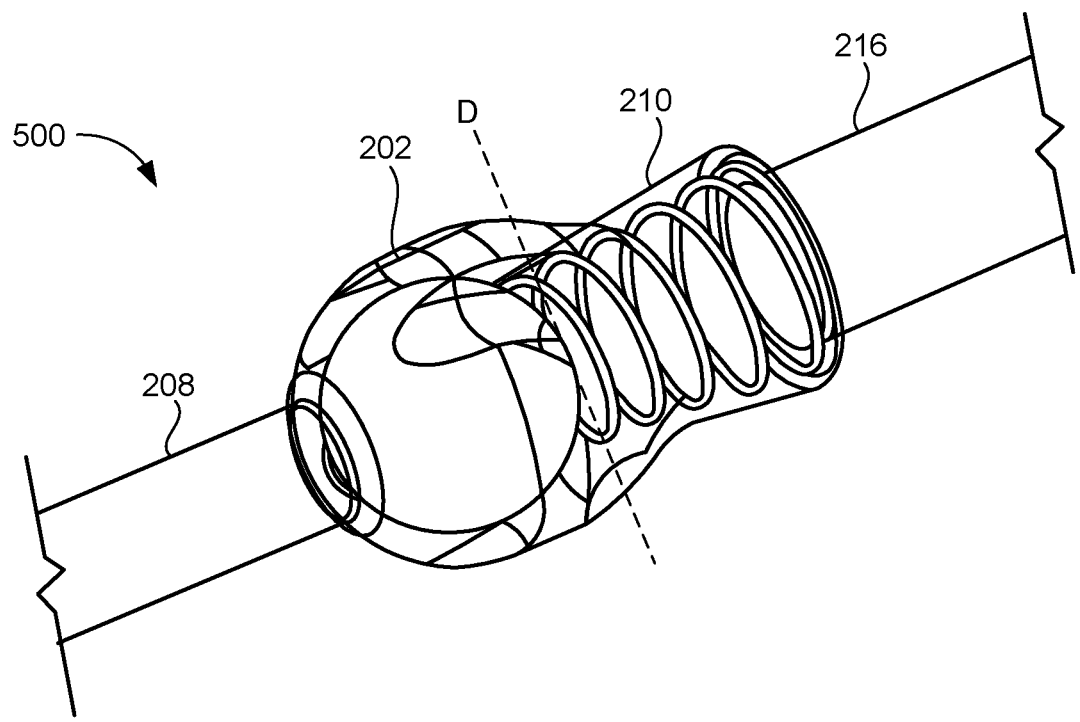
FIG. 5C illustrates the valve of FIGS. 5A and 5B according to an aspect.

FIG. 5C illustrates the valve 500 of FIGS. 5A and 5B according to an aspect. In this example, the landing portions 502A, 502B and channel portions 504A, 504B extend in a direction parallel to the longitudinal exit axis 212 (not labeled in FIG. 5C).

Figure 5D:
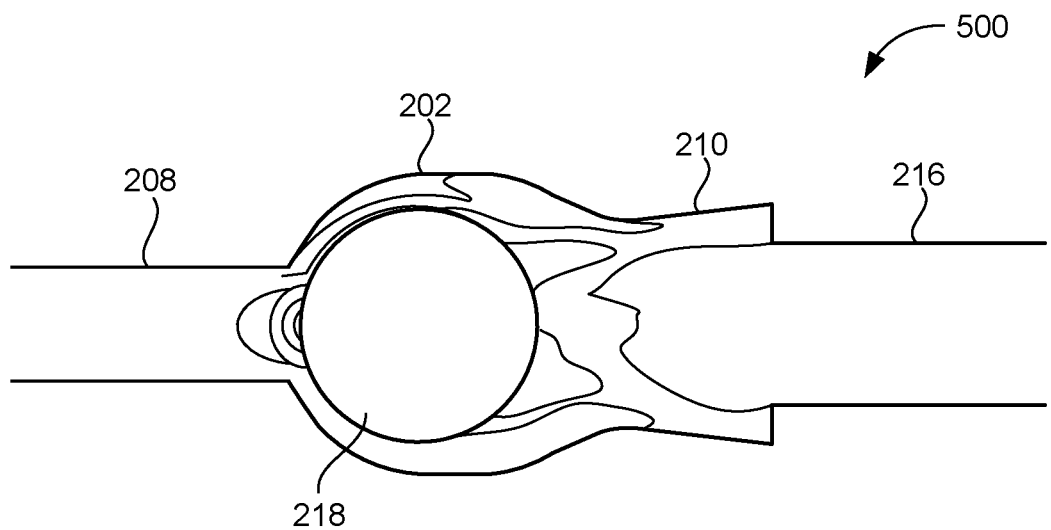
FIG. 5D illustrates the valve of FIGS. 5A, 5B, and 5C according to an aspect.

FIG. 5D illustrates the valve 500 of FIGS. 5A, 5B, and 5C according to an aspect. In this example, the valve member 218 is disposed inside the bulb 202.

Figure 6A:
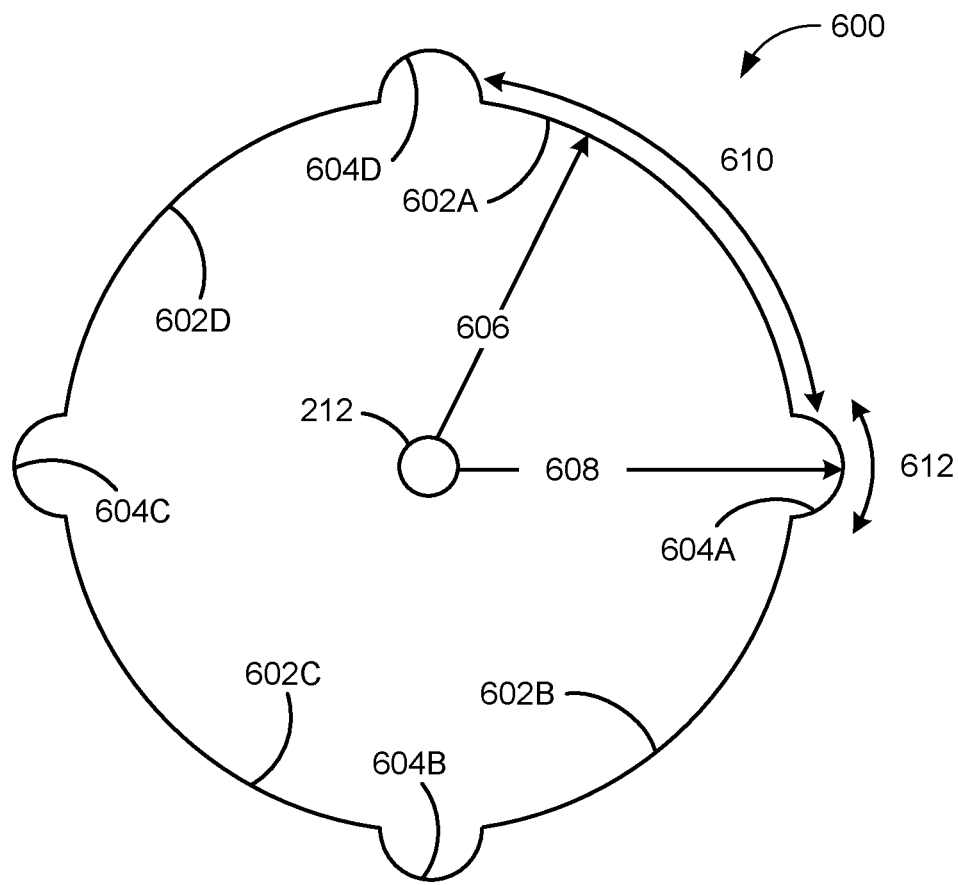
FIG. 6A illustrates a valve according to an aspect.

FIG. 6A illustrates a valve 600 according to an aspect. The valve 600 can include any combination of features of the valve 200 described above. FIG. 6A is a cross-sectional view of the valve 200, 600 along the line denoted 'E' in FIG. 6C. FIG. 6A shows components of the tail 210 and/or exit portion.

The valve 600 and/or tail 210 can include multiple landing portions, such as four landing portions 602A, 602B, 602C, 602D, alternating with multiple channel portions, such as four channel portions 604A, 604B, 604C, 604D. a first landing portion 602A and a second landing portion 602B. The channel portions 604A, 604B, 604C, 604D can define channels (not labeled in FIG. 6A) through which fluid can flow.

In the example shown in FIG. 6A with four landing portions 602A, 602B, 602C, 602D and four channel portions 604A, 604B, 604C, 604D, the first landing portion 602A can be adjacent to, and/or disposed between, the first channel portion 604A and the fourth channel portion 604D. The first channel portion 604A can be adjacent to, and/or disposed between, the first landing portion 604A and the second landing portion 604B. The second landing portion 602B can be adjacent to, and/or disposed between, the first channel portion 604A and the second channel portion 604B. The second channel portion 604B can be adjacent to, and/or disposed between, the second landing portion 604B and the third landing portion 602C. The third landing portion 602C can be adjacent to, and/or disposed between, the second channel portion 604B and the third channel portion 604C. The third channel portion 604C can be adjacent to, and/or disposed between, the third landing portion 604C and the fourth landing portion 602D. The fourth landing portion 602D can be adjacent to, and/or disposed between, the third channel portion 604C and the fourth channel portion 604D. The fourth channel portion 604D can be adjacent to, and/or disposed between, the fourth landing portion 604D and the first landing portion 602A.

When the valve 600 is in the open position, with the valve member 218 and/or poppet resting on and/or pressing against the tail 210 and/or exit portion, the valve member 218 (not labeled in FIG. 6A) can rest on and/or press against the landing portion(s) 602A, 602B, 602C, 602D, and fluid can pass through channels defined by channel portion(s) 604A, 604B, 604C, 604D.

The landing portions 602A, 602B, 602C, 602D can be semicircular about the longitudinal exit axis 212. A distance(s) 608 (labeled only for the first channel portion 604A) of an interior portion(s) of the channel portion(s) 604A, 604B, 604C, 604D from the longitudinal axis 212 can be greater than a distance(s) 606 (labeled only for the first landing portion 602A) of an interior portion(s) of the landing portion(s) 602A, 602B from the longitudinal axis 212, and/or the distance(s) 606 of the interior portion(s) of the landing portion(s) 602A, 602B, 602C, 602D can be less than the distance(s) 606 of the interior portion(s) of the channel portion(s) 604A, 604B, 606C, 606D from the longitudinal axis 212. The greater distance(s) of the interior portion(s) of the channel portion(s) 604A, 604B, 606C, 606D creates and/or defines the channel(s) for the fluid to flow through.

In some examples, a radius, and/or distance 606 from the longitudinal exit axis 212, of the inner portion of the first landing portion 602A, can be equal to a radius, and/or distance from the longitudinal exit axis 212, of the inner portion of the second landing portion 602B, third landing portion 602C, and/or fourth landing portion 602D. In some examples, an arc 610 (labeled only for the first landing portion 602A) of the first landing portion 610A can be equal to an arc of the second landing portion 602B, third landing portion 602C, and/or fourth landing portion 602D. In some examples, the arcs 610 of the landing portion 602A, 602B, 602C, 602D can be greater than arcs 612 (labeled only for the first channel portion 604A) of the channel portions 604A, 604B, 604C, 604D. In some examples, the arcs 610 of the landing portions 602A, 602B, 602C, 602D can have equal lengths and/or circumferences. In some examples, the arcs 612 of the channel portions 604A, 604B, 604C, 604D can have equal lengths and/or circumferences. In some examples, the arc(s) 610 of the landing portions 602A, 602B, 602C, 602D can each be less than one ninety degrees (90°). In some examples, the arc(s) 610 of the landing portions 602A, 602B, 602C, 602D can each be greater than ninety degrees (45°).

In some examples, any combination of the landing portions(s) 602A, 602B and/or channel portions(s) 604A, 604B can curve with respect to the longitudinal exit axis 212. The curving of the landing portions(s) 602A, 602B and/or channel portions(s) 604A, 604B with respect to the longitudinal exit axis 212 can cause the channel portion(s) 604A, 604B to have a vortex and/or spiral shape.

Figure 6B:
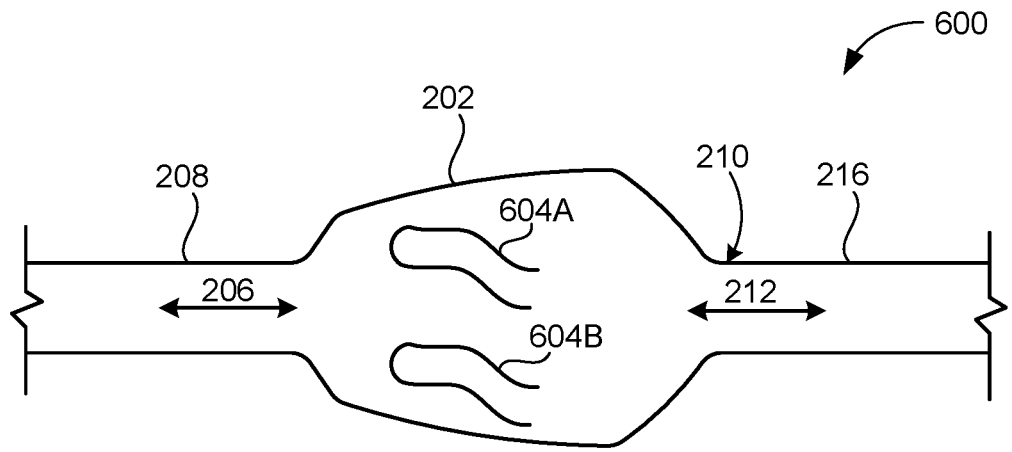
FIG. 6B illustrates the valve of FIG. 6A according to an aspect.

FIG. 6B illustrates the valve 600 of FIG. 6A according to an aspect. FIG. 6B shows the first and second channel portions 604A, 604B curving with respect to the longitudinal exit axis 212. The channel portions 604A, 604B, 604C, 604C can extend within the bulb 202 and/or tail portion 210.

Figure 6C:
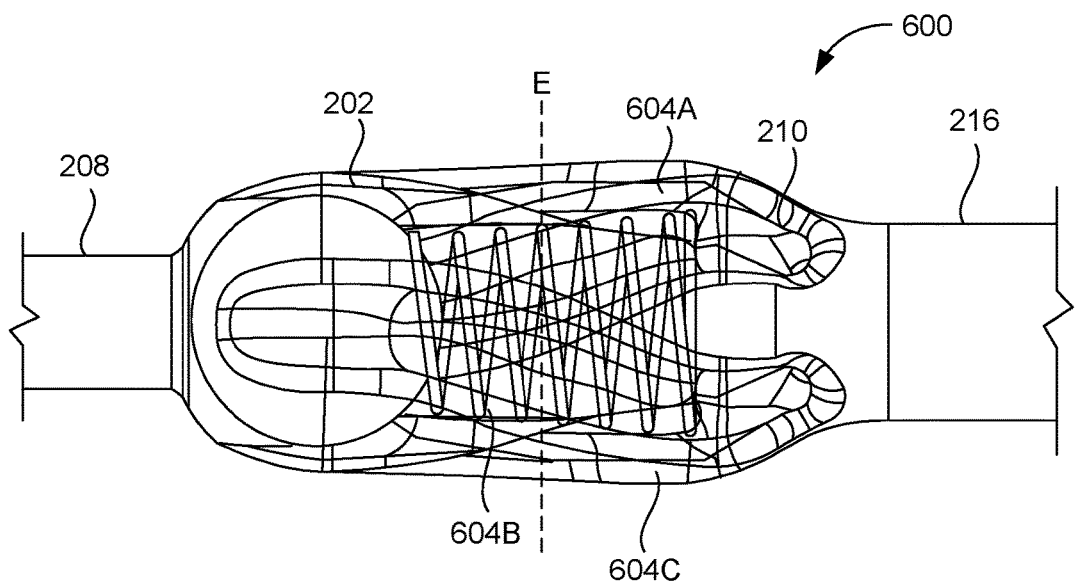
FIG. 6C illustrates the valve of FIGS. 6A and 6B according to an aspect.

FIG. 6C illustrates the valve 600 of FIGS. 6A and 6B according to an aspect. FIG. 6C shows the first, second, and third channel portions 604A, 604B, 604C curving with respect to the longitudinal exit axis (not labeled in FIG. 6C).

Figure 6D:
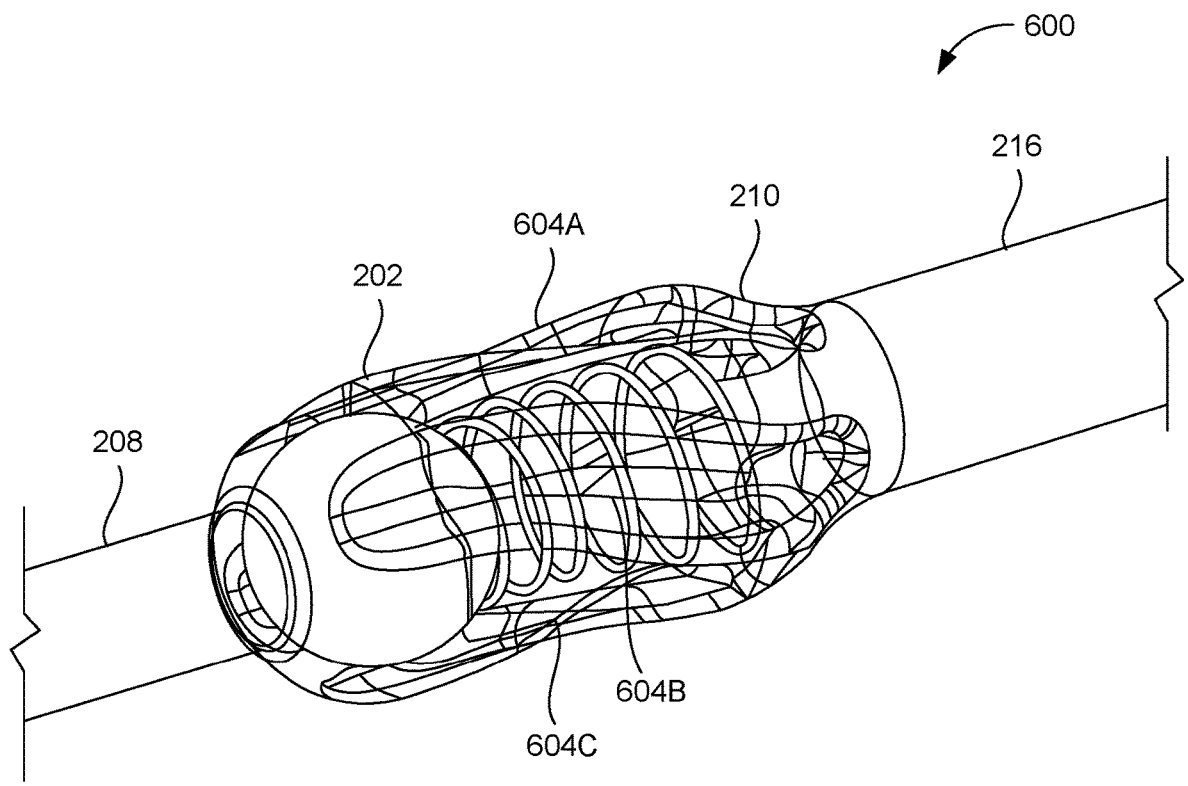
FIG. 6D illustrates the valve of FIGS. 6A, 6B, and 6C according to an aspect.

FIG. 6D illustrates the valve 600 of FIGS. 6A, 6B, and 6C according to an aspect. FIG. 6D shows the first, second, and third channel portions 604A, 604B, 604C curving with respect to the longitudinal exit axis (not labeled in FIG. 6D).

Figure 6E:
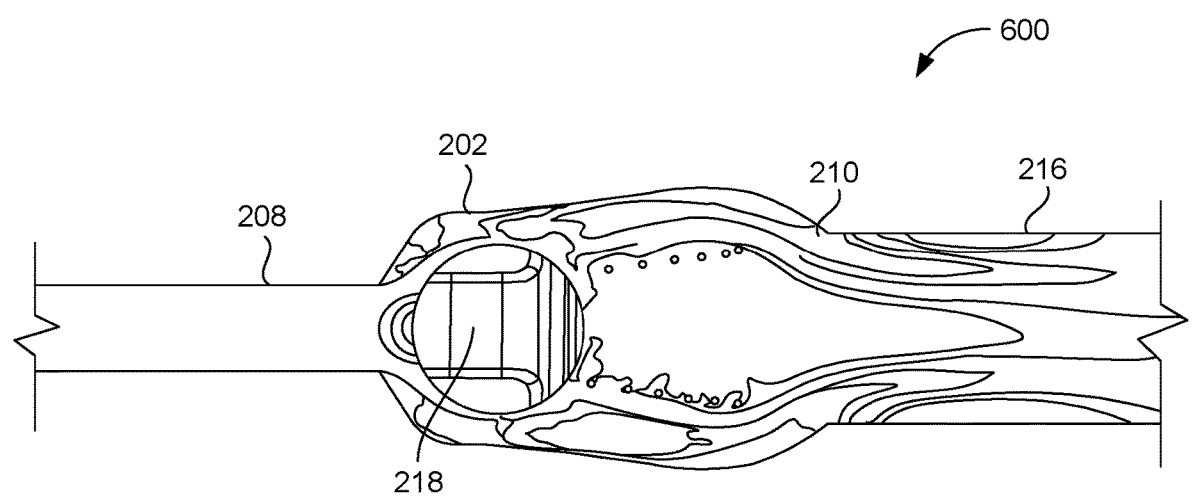
FIG. 6E illustrates the valve of FIGS. 6A, 6B, 6C, and 6D according to an aspect.

FIG. 6E illustrates the valve 600 of FIGS. 6A, 6B, 6C, and 6D according to an aspect. FIG. 6E shows the valve member 218 disposed within the bulb 202. Fluid can flow from the entry tube interface 208, around the valve member 218 and through the bulb 202, and through the tail 210 and exit tube interface 216.

Figure 7A:
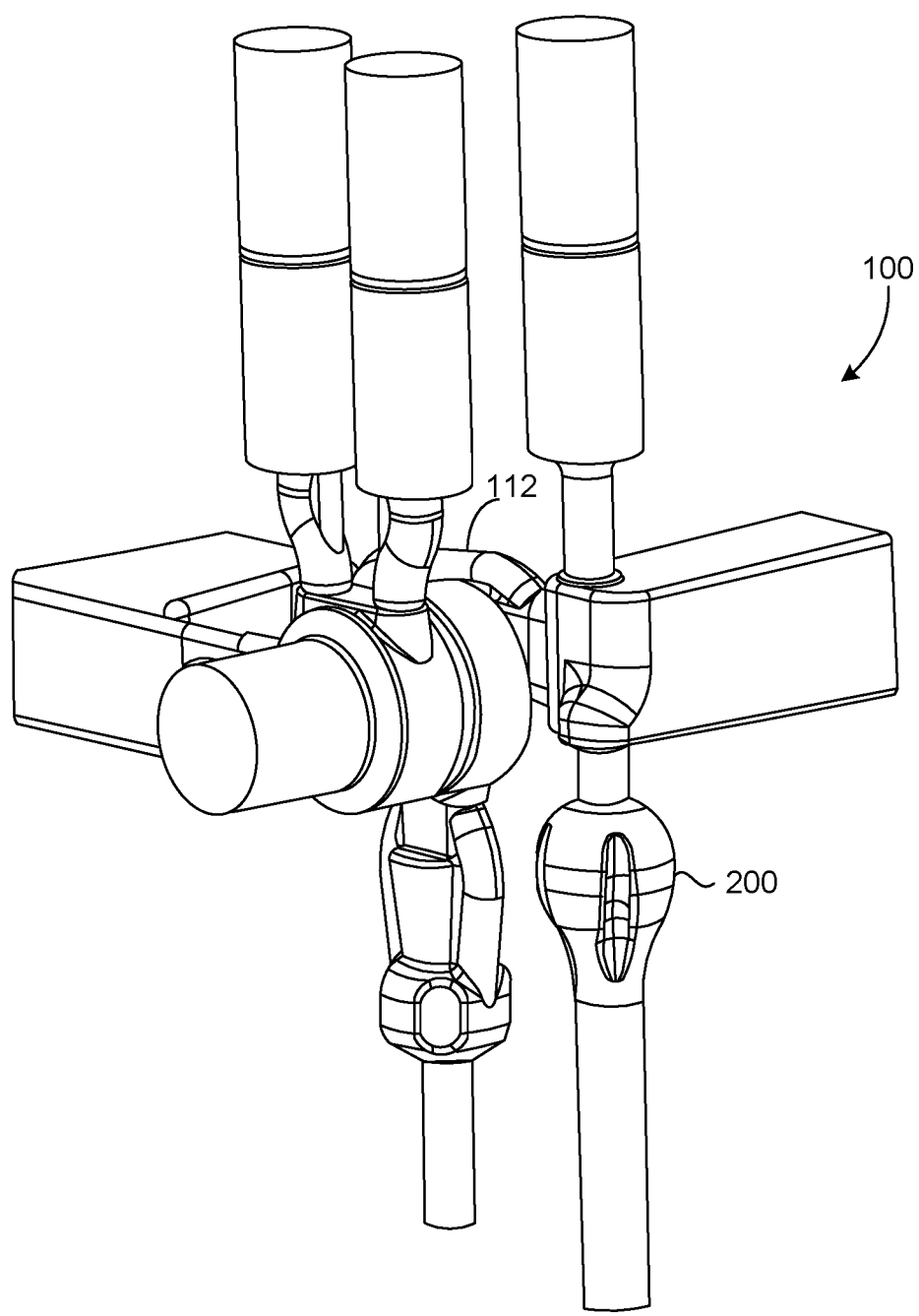
FIG. 7A illustrates a hydraulic system including a valve according to an aspect.

FIG. 7A illustrates a hydraulic system including a valve 200 according to an aspect. FIG. 7A also shows an example location of the deflation valve 112 with respect to the valve 200. The hydraulic system can include any combination of features of the inflatable penile prosthesis 100 described above. The valve 200 can include any combination of features of the valves 200, 300, 400, 500, 600 described above.

Figure 7B:
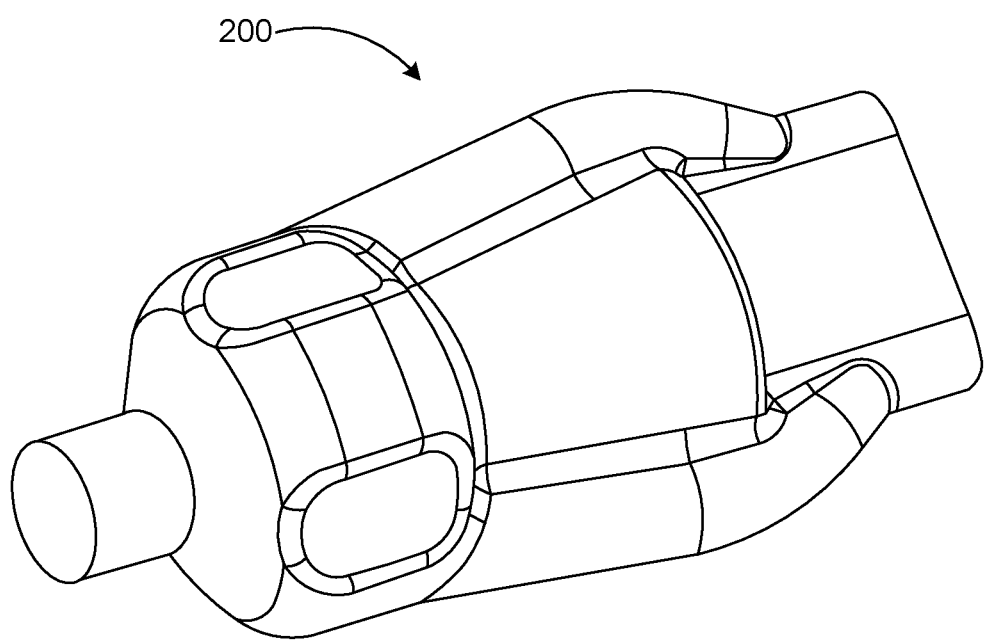
FIG. 7B illustrates a valve according to an aspect.

FIG. 7B illustrates a valve according to an aspect. The valve 200 can include any combination of features of the valves 200, 300, 400, 500, 600 described above.

Figure 7C:
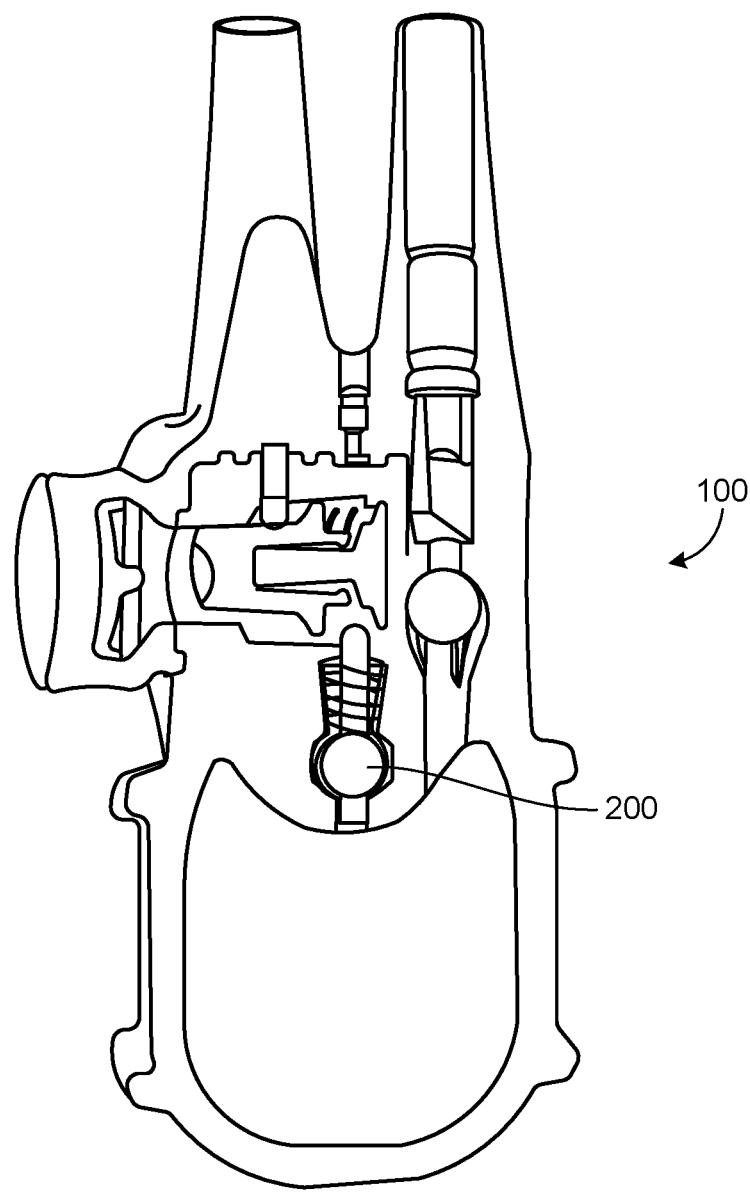
FIG. 7C illustrates a valve according to an aspect.

FIG. 7C illustrates a valve 200 according to an aspect. The valve 200 can include any combination of features of the valves 200, 300, 400, 500, 600 described above. The valve 200 can be included in the inflatable penile prosthesis 100.

Figure 8A:
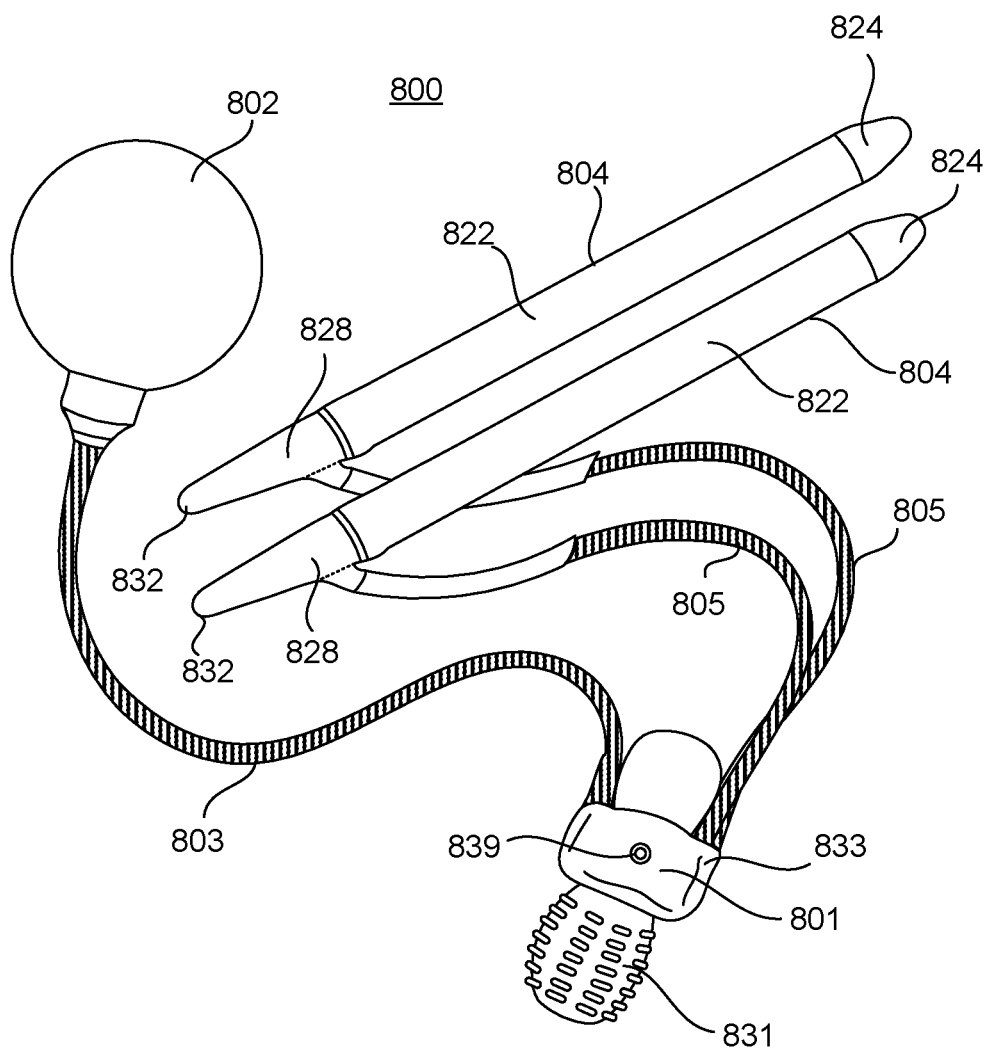
FIG. 8A illustrates a penile prosthesis according to another aspect.
Figure 8B:
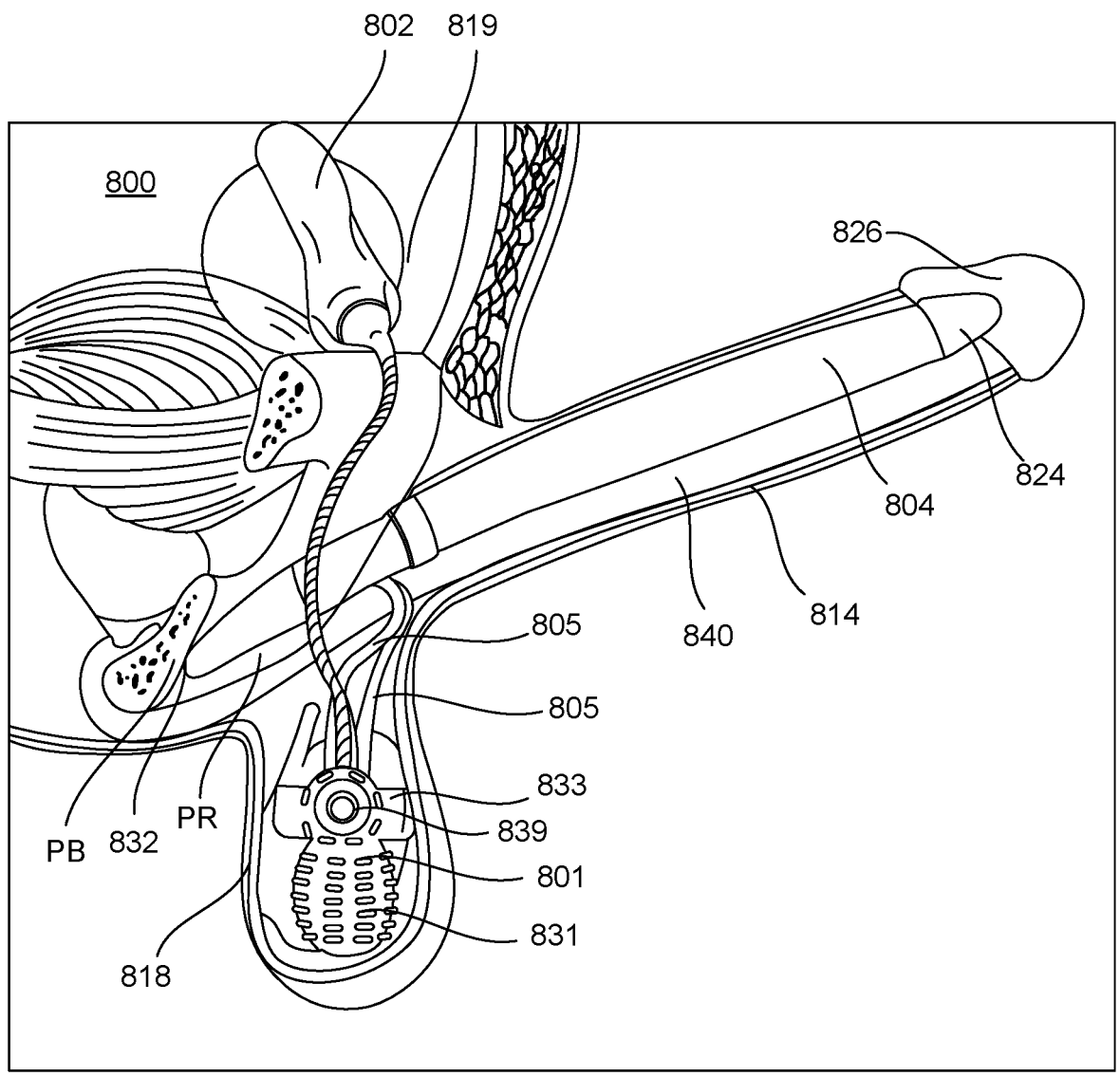
FIG. 8B illustrates a penile prosthesis placed within a body of a patient according to an aspect.

FIG. 8A illustrates a penile prosthesis 800 according to another aspect. FIG. 8B illustrates a penile prosthesis 800 placed within a body of a patient according to an aspect. The penile prosthesis 800 can be an example of the penile prosthesis 100 described with respect to FIG. 1. The penile prosthesis 800 may include a pair of cylinders 804, and the pair of cylinders 804 or inflatable members are implanted in a penis 814. For example, one of the cylinders 804 may be disposed on one side of the penis 814. The other cylinder 804 (not shown in FIG. 8B) of the pair of cylinders may be disposed on the other side of the penis 814. The cylinder 804 may include a first end portion 824, a cavity or inflation chamber 822, and a second end portion 828 having a rear tip 832.

The penile prosthesis 800 may include a pump assembly 801, which may be implanted into the patient's scrotum 818. A pair of conduit connectors 805 may attach the pump assembly 801 to the pair of inflatable members or cylinders 804 such that the pump assembly 801 is in fluid communication with the pair of inflatable members or cylinders 804. Also, the pump assembly 801 may be in fluid communication with a reservoir 802 via a conduit connector 803. The reservoir 802 may be implanted into the patient's abdomen 819. The inflation chamber 822 or portion of the cylinder 804 may be disposed within the penis 814. The first end portion 824 of the cylinder 804 may be at least partially disposed within the crown portion 826 of the penis 814. The second end portion 828 may be implanted into the patient's pubic region PR with the rear tip 832 proximate the pubic bone PB.

In order to implant the inflatable members or cylinders 804, the surgeon first prepares the patient. The surgeon often makes an incision in the penoscrotal region, e.g., where the base of the penis 814 meets with the top of the scrotum 818. From the penoscrotal incision, the surgeon may dilate the patient's corpus cavernosae 840 to prepare the patient to receive the pair of inflatable members or cylinders 804. The corpus cavernosum is one of two parallel columns of erectile tissue forming the dorsal part of the body of the penis 814, e.g., two slender columns that extend substantially the length of the penis 814. The surgeon will also dilate two regions of the pubic area to prepare the patient to receive the second end portion 828. The surgeon may measure the length of the corpora cavernosae from the incision and the dilated region of the pubic area to determine an appropriate size of the inflatable members or cylinders 804 to implant.

After the patient is prepared, the penile prosthesis 800 is implanted into the patient. The tip of the first end portion 824 of each cylinder 804 may be attached to a suture. The other end of the suture may be attached to a needle member (e.g., Keith needle). The needle member is inserted into the incision and into the dilated corpus cavernosum. The needle member is then forced through the crown of the penis 814. The surgeon tugs on the suture to pull the cylinder 804 into the corpus cavernosum. This is done for each cylinder of the pair of cylinders 804. Once the inflation chamber 822 is in place, the surgeon may remove the suture from the tip. The surgeon then inserts the second end portion 828. The surgeon inserts the rear end of the cylinder 804 into the incision and forces the second end portion 828 toward the pubic bone PB until each cylinder 804 is in place.

The pump assembly 801 includes a pump bulb 831, a valve body 833, and a selection member 839. The selection member 839 may be used to select or change the mode of the pump assembly 801. For example, the selection member 839 may be moved from a first position to a second position to place the device in its deflation mode. The selection member 839 may then be moved back from the second position to the first position to place the device in the inflation mode. In some embodiments, the selection member 839 is movable with respect to the valve body 833.

The pump bulb 831 may be squeezed or depressed by the patient in order to facilitate the transfer of fluid from the reservoir 802 to the cylinders 804. For example, in the inflation mode, while the patient is operating the pump bulb 831, the pump bulb 831 may receive the fluid from the reservoir 802, and then output the fluid to the cylinders 804. When the patient switches to the deflation mode, at least some of the fluid can automatically be transferred back to the reservoir 802 (due to the difference in pressure from the cylinders 804 to the reservoir 802). Then, the patient may squeeze the cylinders 804 to facilitate the further transfer of fluid through the pump bulb 831 to the reservoir 802.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An inflatable penile prosthesis comprising:
    a reservoir configured to hold fluid;
    an inflatable member; and
    a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:
        an entry portion defining an entry portion passageway;
        a middle portion adjacent to the entry portion, the middle portion being wider than the entry portion and defining a chamber;
        an exit portion adjacent to the middle portion, the exit portion being narrower than the middle portion, the exit portion defining an exit portion passageway and comprising:
            a first landing portion extending non-linearly along a length of the middle portion and including an interior portion, the interior portion of the first landing portion being semicircular about a longitudinal exit axis, the longitudinal exit axis extending through a center of the exit portion parallel to a direction that an exit tube interface extends from the exit portion, and
            a first channel portion adjacent to the first landing portion and including an interior portion, the interior portion of the first channel portion being farther from the longitudinal exit axis than the interior portion of the first landing portion;
        the exit tube interface adjacent to the exit portion, the exit tube interface being configured to attach to the exit tube, the exit tube interface being narrower than the middle portion, the exit tube interface defining an exit passageway; and
        a valve member disposed inside the chamber, the valve member being biased to rest against the entry portion.

2. The inflatable penile prosthesis of claim 1, wherein the at least one valve further comprises an entry tube interface adjacent to the entry portion, the entry tube interface being configured to attach to the entry tube and defining an entry passageway.

3. The inflatable penile prosthesis of claim 2, wherein:
    the at least one valve includes an inflation valve configured to transfer fluid from the pump assembly to the inflatable member;
    the entry tube is attached to the pump bulb and to the entry tube interface of the inflation valve; and
    the exit tube is attached to the inflatable member and to the exit tube interface of the inflation valve.

4. The inflatable penile prosthesis of claim 1, wherein the entry portion is circular about a longitudinal entry portion, the longitudinal entry portion axis being parallel to a direction from which the entry tube interface extends from the entry portion.

5. The inflatable penile prosthesis of claim 1, wherein the exit portion further comprises:
    a second landing portion adjacent to the first channel portion and including an interior portion, the interior portion of the second landing portion being semicircular about the longitudinal exit axis and having a landing radius about the longitudinal exit axis that is equal to a landing radius of the first landing portion; and a second channel portion adjacent to the first landing portion and the second landing portion and including an interior portion, the interior portion of the second channel portion being farther from the longitudinal exit axis than the interior portion of the first landing portion.

6. The inflatable penile prosthesis of claim 5, wherein:
the interior portion of the first landing portion has a first landing arc about the longitudinal exit axis;
the interior portion of the second landing portion has a second landing arc about the longitudinal exit axis; and
the first landing arc is equal to the second landing arc.

7. The inflatable penile prosthesis of claim 5, wherein:
the interior portion of the first landing portion has a first landing arc about the longitudinal exit axis;
the interior portion of the second landing portion has a second landing arc about the longitudinal exit axis; and
the first landing arc is greater than the second landing arc.

8. The inflatable penile prosthesis of claim 1, wherein:
the interior portion of the first landing portion has a landing arc about the longitudinal exit axis;
the interior portion of the first landing portion has a landing radius about the longitudinal exit axis;
the interior portion of the first channel portion is semicircular about the longitudinal exit axis;
the interior portion of the first channel portion has a channel arc that is less than the landing arc of the first landing portion; and
the interior portion of the first channel portion has a channel radius about the longitudinal exit axis that is greater than the landing radius of the first landing portion.

9. The inflatable penile prosthesis of claim 8, wherein the landing arc is less than one hundred eighty degrees (180°).

10. The inflatable penile prosthesis of claim 8, wherein the landing arc is greater than ninety degrees (90°).

11. The inflatable penile prosthesis of claim 1, wherein the at least one valve includes a refill valve configured to transfer fluid from the reservoir to the pump bulb.

12. The inflatable penile prosthesis of claim 1, wherein the at least one valve further includes a biasing member, the biasing member biasing the valve member to rest against the entry portion.

13. The inflatable penile prosthesis of claim 1, wherein the at least one valve further includes a spring, the spring biasing the valve member to rest against the entry portion.

14. The inflatable penile prosthesis of claim 1, wherein the interior portions of the first landing portion and the first channel portion and extend into the middle portion in a direction parallel to the longitudinal exit axis.

15. The inflatable penile prosthesis of claim 1, wherein the interior portions of the first landing portion and the first channel portion extend into the middle portion along paths that curve with respect to the longitudinal exit axis.

16. An inflatable penile prosthesis comprising:
a reservoir configured to hold fluid;
an inflatable member; and
a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:
an entry portion defining an entry portion passageway;
a middle portion adjacent to the entry portion, the middle portion being wider than the entry portion and defining a chamber;
an exit portion adjacent to the middle portion, the exit portion being narrower than the middle portion, the exit portion defining an exit portion passageway and comprising:
a first landing portion extending non-linearly along a length of the middle portion and including an interior portion, the interior portion of the first landing portion being semicircular about a longitudinal exit axis, the longitudinal exit axis extending through a center of the exit portion parallel to a direction that an exit tube interface extends from the exit portion, the interior portion of the first landing portion having a landing arc;
a first channel portion adjacent to the first landing portion and including an interior portion, the interior portion of the first channel portion being farther from the longitudinal exit axis than the interior portion of the first landing portion, the interior portion of the first channel portion having a channel arc, the channel arc of the first channel portion being less than the landing arc of the first landing portion, the first channel portion extending into the middle portion in a direction parallel to the longitudinal exit axis;
a second landing portion adjacent to the first channel portion and including an interior portion, the interior portion of the second landing portion being semicircular about the longitudinal exit axis and having a landing arc that is equal to the landing arc of the interior portion of the first landing portion; and
a second channel portion adjacent to the second landing portion and the first landing portion and including an interior portion, the interior portion of the second channel being farther from the longitudinal exit axis than the interior portion of the first landing portion and the interior portion of second landing portion, the interior portion of the second channel portion having a channel arc that is equal to the channel arc of the first channel portion, the second channel portion extending into the middle portion in a direction parallel to the longitudinal exit axis;
the exit tube interface adjacent to the exit portion, the exit tube interface being configured to attach to the exit tube, the exit tube interface being narrower than the middle portion, the exit tube interface defining an exit passageway; and
a valve member disposed inside the chamber, the valve member being biased to rest against the entry portion.

17. The inflatable penile prosthesis of claim 16, wherein the at least one valve further includes a biasing member, the biasing member biasing the valve member to rest against the entry portion.

18. The inflatable penile prosthesis of claim 16, wherein the valve member is sphere shaped.

19. An inflatable penile prosthesis comprising:
a reservoir configured to hold fluid;
an inflatable member; and
a pump assembly configured to transfer fluid from the reservoir to the inflatable member, the pump assembly comprising a pump bulb, at least one valve, an entry tube configured to provide the fluid to the at least one valve, and an exit tube configured to send the fluid from the at least one valve, the pump bulb being configured to transfer the fluid from the reservoir, through the at least one valve, and to the inflatable member in response to the pump bulb being compressed, the at least one valve comprising:
an entry portion defining an entry portion passageway;
a middle portion adjacent to the entry portion, the middle portion being wider than the entry portion and defining a chamber;
an exit portion adjacent to the middle portion, the exit portion being narrower than the middle portion, the exit portion defining an exit portion passageway and comprising:
  a first landing portion extending non-linearly along a length of the middle portion and including an interior portion, the interior portion of the first landing portion being semicircular about a longitudinal exit axis, the longitudinal exit axis extending through a center of the exit portion parallel to a direction that an exit tube interface extends from the exit portion, the interior portion of the first landing portion having a landing arc;
  a first channel portion adjacent to the first landing portion and including an interior portion, the interior portion of the first channel portion being farther from the longitudinal exit axis than the interior portion of the first landing portion, the interior portion of the first channel portion having a channel arc, the channel arc of the first channel portion being less than the landing arc of the first landing portion, the first channel portion extending into the middle portion along a path that curves with respect to the longitudinal exit axis;
  a second landing portion adjacent to the first channel portion and including an interior portion, the interior portion of the second landing portion being semicircular about the longitudinal exit axis and having a landing arc that is equal to the landing arc of the interior portion of the first landing portion; and
  a second channel portion adjacent to the second landing portion and the first landing portion and including an interior portion, the interior portion of the second channel being farther from the longitudinal exit axis than the interior portion of the first landing portion and the interior portion of second landing portion, the interior portion of the second channel portion having a channel arc that is equal to the channel arc of the first channel portion, the second channel portion extending into the middle portion along a path that curves with respect to the longitudinal exit axis;
the exit tube interface adjacent to the exit portion, the exit tube interface being configured to attach to the exit tube, the exit tube interface being narrower than the middle portion, the exit tube interface defining an exit passageway; and
a valve member disposed inside the chamber, the valve member being biased to rest against the entry portion.

20. The inflatable penile prosthesis of claim 19, wherein the at least one valve further includes a biasing member, the biasing member biasing the valve member to rest against the entry portion.

* * * * *